US010213373B2

(12) United States Patent
Loupis et al.

(10) Patent No.: US 10,213,373 B2
(45) Date of Patent: *Feb. 26, 2019

(54) CHROMOPHORE COMBINATIONS FOR BIOPHOTONIC USES

(71) Applicant: KLOX Technologies Inc., Laval (CA)

(72) Inventors: Nikolaos Loupis, Athens (GR); Remigio Piergallini, Grottammare Ascoli Piceno (IT)

(73) Assignee: KLOX TECHNOLOGIES, INC., Laval, Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/427,993

(22) PCT Filed: Sep. 13, 2013

(86) PCT No.: PCT/CA2013/000786

§ 371 (c)(1),
(2) Date: Mar. 12, 2015

(87) PCT Pub. No.: WO2014/040176

PCT Pub. Date: Mar. 20, 2014

(65) Prior Publication Data

US 2015/0246127 A1   Sep. 3, 2015

(30) Foreign Application Priority Data

Apr. 19, 2013 (GB) .................................. 1307157.6
Apr. 19, 2013 (WO) ................ PCT/CA2013/000395

(51) Int. Cl.
| | | |
|---|---|---|
| *A61K 8/49* | (2006.01) | |
| *A61K 41/00* | (2006.01) | |
| *A61N 5/06* | (2006.01) | |
| *A61Q 19/08* | (2006.01) | |
| *A61K 8/04* | (2006.01) | |
| *A61K 8/22* | (2006.01) | |
| *A61Q 19/00* | (2006.01) | |
| *A61K 8/81* | (2006.01) | |
| *A61Q 19/02* | (2006.01) | |

(52) U.S. Cl.
CPC .............. *A61K 8/498* (2013.01); *A61K 8/042* (2013.01); *A61K 8/22* (2013.01); *A61K 8/8147* (2013.01); *A61K 41/00* (2013.01); *A61K 41/0057* (2013.01); *A61N 5/06* (2013.01); *A61N 5/062* (2013.01); *A61N 5/0616* (2013.01); *A61Q 19/00* (2013.01); *A61Q 19/02* (2013.01); *A61Q 19/08* (2013.01); *A61K 2800/262* (2013.01); *A61K 2800/434* (2013.01); *A61K 2800/5922* (2013.01); *A61K 2800/81* (2013.01); *A61N 2005/0645* (2013.01); *A61N 2005/0647* (2013.01); *A61N 2005/0662* (2013.01); *A61N 2005/0663* (2013.01)

(58) Field of Classification Search
CPC .......... A61K 2800/434; A61K 2800/81; A61K 8/498; A61K 2800/262; A61K 2800/5922; A61K 41/0057; A61K 8/042; A61K 8/22; A61K 41/00; A61K 8/8147; A61N 5/062; A61N 2005/0662; A61N 5/0616; A61N 2005/0645; A61N 2005/0647; A61N 2005/0663; A61N 5/06; A61Q 19/08; A61Q 19/00; A61Q 19/02
USPC ............................. 514/454; 604/20; 607/88
See application file for complete search history.

(56) References Cited

U.S. PATENT DOCUMENTS

| | | | |
|---|---|---|---|
| 2,877,221 A | 3/1959 | Lanbach | |
| 3,293,127 A | 12/1966 | Beck | |
| 3,309,274 A | 3/1967 | Brilliant | |
| 3,372,125 A | 3/1968 | Hill | |
| 3,595,798 A | 7/1971 | Smith et al. | |
| 3,597,362 A | 8/1971 | Rauhut et al. | |
| 3,652,420 A | 3/1972 | Hill | |
| 3,671,450 A | 6/1972 | Rauhut et al. | |
| 3,728,446 A | 4/1973 | Roberts et al. | |
| 4,320,140 A | 3/1982 | Crounse et al. | |
| 4,574,097 A | 3/1986 | Honeycutt | |
| 4,647,578 A | 3/1987 | Crounse et al. | |
| 4,891,211 A | 1/1990 | Winston | |
| 4,992,256 A | 2/1991 | Skaggs et al. | |
| 5,292,362 A | 3/1994 | Bass et al. | |
| 5,611,793 A | 3/1997 | Wilson et al. | |
| 5,658,148 A | 8/1997 | Neuberger et al. | |
| 5,723,148 A | 3/1998 | Love | |
| 5,749,968 A | 5/1998 | Melanson et al. | |
| 5,785,527 A | 7/1998 | Jensen et al. | |

(Continued)

FOREIGN PATENT DOCUMENTS

| | | |
|---|---|---|
| CA | 2166527 A1 | 7/1996 |
| CA | 2222027 A1 | 6/1998 |

(Continued)

OTHER PUBLICATIONS

IPRP/WO dated Jan. 8, 2014 for PCT/CA2013/000786.
Alster, et al., "Photodynamic therapy: practical cosmetic applications," Journal of Drugs in Dermatology, 5(8):764-768 (2006).
Antunes, et al., "Evaluation of the clastogenicity and anticlastongenicity of the carotenoid bixin in human lymphocyte cultures," Mutation Research, 585(1-2):113-9 (2005).
Ariizumi et al., "Clinical evaluation of a topical applicant TSG-88 for periodontal disease," Dental Drug Therapy, 10(2):157-168 (1991) (English Abstract included).
Berneburg, et al., "Phototherapy with narrowband UVB," Acta Dermato-Venereologica, 85:1-11 (2005).

(Continued)

Primary Examiner — My-Chau T. Tran
(74) Attorney, Agent, or Firm — BCF LLP

(57) ABSTRACT

The present disclosure provides biophotonic compositions and methods useful in phototherapy. In particular, the biophotonic compositions of the present disclosure comprise at least two xanthene dyes. The biophotonic compositions and the method of the disclosure are useful for promoting wound healing and skin rejuvenation, as well as treating acne and other skin conditions.

16 Claims, 16 Drawing Sheets

(56) References Cited

U.S. PATENT DOCUMENTS

| | | |
|---|---|---|
| 5,844,016 A | 12/1998 | Sawhney et al. |
| 5,858,332 A | 1/1999 | Jensen et al. |
| 5,922,331 A | 7/1999 | Mausner |
| 6,107,466 A | 8/2000 | Hasan et al. |
| 6,121,341 A | 9/2000 | Sawhney et al. |
| 6,149,895 A | 11/2000 | Kutsch |
| 6,444,725 B1 | 9/2002 | Trom et al. |
| 6,485,709 B2 | 11/2002 | Banerjee et al. |
| 6,541,460 B2 | 4/2003 | Petito |
| 6,905,672 B2 | 6/2005 | Rajaiah et al. |
| 7,066,941 B2 | 6/2006 | Perricone |
| 7,081,128 B2 | 7/2006 | Hart et al. |
| 7,255,691 B2 * | 8/2007 | Tolkoff .................. A61N 5/06 313/483 |
| 7,314,470 B2 | 1/2008 | Malodobry |
| 7,354,448 B2 | 4/2008 | Altshuler et al. |
| 8,075,875 B2 | 12/2011 | Piergallini et al. |
| 8,182,473 B2 | 5/2012 | Altshuler et al. |
| 8,632,822 B2 * | 1/2014 | Piergallini .......... A61K 31/352 424/616 |
| 8,637,086 B2 * | 1/2014 | Piergallini .......... A61K 31/352 424/616 |
| 8,658,219 B2 * | 2/2014 | Piergallini .......... A61K 31/352 424/616 |
| 8,685,466 B2 | 4/2014 | Piergallini et al. |
| 8,911,791 B2 * | 12/2014 | Piergallini .......... A61K 31/352 424/616 |
| 8,974,833 B2 * | 3/2015 | Piergallini .......... A61K 31/352 424/616 |
| 8,986,719 B2 | 3/2015 | Piergallini et al. |
| 8,986,745 B2 * | 3/2015 | Piergallini .......... A61K 31/352 424/616 |
| 8,986,746 B2 | 3/2015 | Piergallini et al. |
| 9,345,648 B2 | 5/2016 | Piergallini et al. |
| 9,375,446 B2 * | 6/2016 | Piergallini .......... A61K 31/352 |
| 9,375,466 B2 | 6/2016 | Piergallini et al. |
| 2001/0022970 A1 | 9/2001 | Dees et al. |
| 2002/0029071 A1 | 3/2002 | Whitehurst |
| 2003/0004499 A1 | 1/2003 | McDaniel |
| 2003/0198605 A1 | 10/2003 | Montgomery |
| 2004/0010299 A1 | 1/2004 | Tolkoff |
| 2004/0136971 A1 | 7/2004 | Scharp et al. |
| 2004/0147984 A1 | 7/2004 | Altshuler et al. |
| 2004/0191330 A1 | 9/2004 | Keefe et al. |
| 2004/0193234 A1 | 9/2004 | Butler |
| 2004/0262569 A1 | 12/2004 | Cho et al. |
| 2005/0026298 A1 | 2/2005 | Bickett et al. |
| 2005/0042712 A1 | 2/2005 | Huth et al. |
| 2005/0059731 A1 | 3/2005 | Albrecht et al. |
| 2005/0098766 A1 | 5/2005 | Watson |
| 2005/0123588 A1 | 6/2005 | Zhu et al. |
| 2005/0261750 A1 | 11/2005 | McDaniel |
| 2006/0199242 A1 | 9/2006 | Cheung et al. |
| 2006/0217690 A1 | 9/2006 | Bastin et al. |
| 2006/0251687 A1 | 11/2006 | Lapidot et al. |
| 2007/0021807 A1 | 1/2007 | Kurtz |
| 2007/0092469 A1 | 4/2007 | Jacobs |
| 2007/0128132 A1 | 6/2007 | Piergallini et al. |
| 2007/0166369 A1 | 7/2007 | Neuberger et al. |
| 2007/0191249 A1 | 8/2007 | Lant |
| 2007/0244195 A1 | 10/2007 | Burkhart et al. |
| 2008/0058689 A1 | 3/2008 | Holloway et al. |
| 2008/0091250 A1 | 4/2008 | Powell |
| 2008/0096857 A1 | 4/2008 | Curaudeau et al. |
| 2008/0108681 A1 | 5/2008 | Scimeca et al. |
| 2008/0113037 A1 | 5/2008 | Green et al. |
| 2008/0118578 A1 | 5/2008 | Dees |
| 2008/0206159 A1 | 8/2008 | Tamarkin |
| 2008/0255498 A1 | 10/2008 | Houle |
| 2008/0305101 A1 | 12/2008 | Ruoslahti et al. |
| 2009/0088824 A1 | 4/2009 | Baird et al. |
| 2010/0227799 A1 * | 9/2010 | Trudel ................ A61K 31/409 514/19.3 |
| 2010/0255045 A1 | 10/2010 | Eymard Du Vernet |
| 2010/0266989 A1 | 10/2010 | Piergallini et al. |
| 2010/0277105 A1 | 11/2010 | Oyama |
| 2011/0171310 A1 | 7/2011 | Gousse et al. |
| 2011/0319808 A1 | 12/2011 | Godfrey et al. |
| 2012/0171641 A1 | 7/2012 | Piergallini et al. |
| 2013/0122467 A1 | 5/2013 | Piergallini et al. |
| 2013/0281913 A1 | 10/2013 | Piergallini et al. |
| 2014/0105832 A1 | 4/2014 | Loupis et al. |
| 2014/0276354 A1 | 9/2014 | Piergallini et al. |
| 2014/0303547 A1 | 10/2014 | Loupis et al. |
| 2015/0065453 A1 | 3/2015 | Piergallini et al. |
| 2015/0119788 A1 * | 4/2015 | Loupis .................. A61N 5/062 604/20 |
| 2015/0246127 A1 | 9/2015 | Loupis |
| 2015/0290103 A1 | 10/2015 | Piergallini et al. |
| 2015/0290320 A1 | 10/2015 | Piergallini et al. |
| 2015/0306131 A1 | 10/2015 | Piergallini et al. |
| 2015/0360047 A1 | 12/2015 | Loupis et al. |
| 2016/0030564 A1 * | 2/2016 | Loupis ............... A61K 41/0057 604/20 |
| 2016/0136075 A1 | 5/2016 | Loupis et al. |
| 2017/0027833 A1 * | 2/2017 | Piergallini ............. A61K 41/00 |
| 2017/0112755 A1 * | 4/2017 | Piergallini ............. A61K 8/042 |
| 2017/0326378 A1 * | 11/2017 | Loupis .................. A61N 5/062 |

FOREIGN PATENT DOCUMENTS

| | | |
|---|---|---|
| CA | 2360202 A1 | 7/2000 |
| CA | 2457590 A1 | 3/2003 |
| CA | 2551613 | 12/2005 |
| CA | 2580381 A1 | 1/2006 |
| CA | 2706808 A1 | 8/2009 |
| CA | 2742942 A1 | 5/2010 |
| CA | 2742943 A1 | 5/2010 |
| CA | 2745059 A1 | 6/2010 |
| CA | 2809405 A1 | 1/2012 |
| CA | 2868893 A1 | 10/2013 |
| CA | 2883717 A1 | 3/2014 |
| CN | 102133208 A | 7/2011 |
| DE | 2935450 A1 | 3/1981 |
| EP | 0380157 A | 8/1990 |
| EP | 0704539 A2 | 4/1996 |
| EP | 1235543 A1 | 9/2002 |
| EP | 1235544 A1 | 9/2002 |
| EP | 1779891 A1 | 5/2007 |
| EP | 1951184 | 8/2008 |
| EP | 2338465 | 6/2011 |
| JP | 01-279838 | 11/1989 |
| JP | H03169805 A | 7/1991 |
| JP | 04-219756 | 8/1992 |
| JP | H092925 A | 1/1997 |
| JP | H10182390 A | 7/1998 |
| JP | H10330235 | 12/1998 |
| JP | 2001-511137 A | 8/2001 |
| JP | 2002-502864 | 1/2002 |
| JP | 2002-226349 A | 8/2002 |
| JP | 2002233612 A | 8/2002 |
| JP | 2002-293747 A | 10/2002 |
| JP | 2003-339875 A | 12/2003 |
| KR | 102007001729 | 2/2007 |
| WO | WO-1981000513 A1 | 3/1981 |
| WO | WO-1990009779 A1 | 9/1990 |
| WO | WO-1991002530 A1 | 3/1991 |
| WO | WO-1993021992 A1 | 11/1993 |
| WO | WO-1998010738 A1 | 3/1998 |
| WO | WO-1998011827 A1 | 3/1998 |
| WO | WO-1998030169 A1 | 7/1998 |
| WO | WO-1999039238 A1 | 8/1999 |
| WO | WO-1999049823 | 10/1999 |
| WO | WO-1999063900 A1 | 12/1999 |
| WO | WO-2000040266 | 7/2000 |
| WO | WO-2001000190 | 1/2001 |
| WO | WO-01/12181 A1 | 2/2001 |
| WO | WO-2002015539 | 2/2002 |
| WO | WO-2003000215 | 1/2003 |
| WO | WO-2003017824 | 3/2003 |
| WO | WO-2003061696 A2 | 7/2003 |
| WO | WO-2003086215 | 10/2003 |
| WO | WO-2003099247 | 12/2003 |

(56) References Cited

FOREIGN PATENT DOCUMENTS

| | | |
|---|---|---|
| WO | WO-2004028498 | 4/2004 |
| WO | WO-2004081222 A2 | 9/2004 |
| WO | WO-2005009604 A1 | 2/2005 |
| WO | WO-2005051305 A2 | 6/2005 |
| WO | WO-2005112948 | 12/2005 |
| WO | WO-2006014597 A1 | 2/2006 |
| WO | WO-2006032847 A1 | 3/2006 |
| WO | WO-2006047868 A1 | 5/2006 |
| WO | WO-2006072243 A1 | 7/2006 |
| WO | WO-2006118835 A2 | 11/2006 |
| WO | WO-2006125650 A1 | 11/2006 |
| WO | WO-2006135344 A1 | 12/2006 |
| WO | WO-2007025244 A2 | 3/2007 |
| WO | WO-2007080453 A2 | 7/2007 |
| WO | WO-2007087259 A2 | 8/2007 |
| WO | WO-2007127172 A2 | 11/2007 |
| WO | WO-2008011707 A1 | 1/2008 |
| WO | WO-2008013962 A2 | 1/2008 |
| WO | WO-2008052081 A2 | 5/2008 |
| WO | WO-2009089346 A2 | 7/2009 |
| WO | WO-2010/051636 A1 | 5/2010 |
| WO | WO-2010051641 A1 | 5/2010 |
| WO | WO-2010070292 A1 | 6/2010 |
| WO | WO-2011006263 A1 | 1/2011 |
| WO | WO-2011058448 A2 | 5/2011 |
| WO | WO-2011134087 A1 | 11/2011 |
| WO | WO-2012011875 A1 | 1/2012 |
| WO | WO-2012072980 A1 | 6/2012 |
| WO | WO-2013155620 A1 | 10/2013 |
| WO | WO-2014040176 A1 | 3/2014 |
| WO | WO-2014138930 | 9/2014 |
| WO | WO-2015000058 | 1/2015 |

OTHER PUBLICATIONS

Chen et al., "Study of the chemiluminescent characteristics of some xanthone dyes," Analytica Chimica Acta, 292(1-2) (9 pages) (1994).
Clark, et al, "Eosin-Phloxine alcoholic solution," Mitt. Zool. Stat. Neapel, Jan. 1, 1981 (Jan. 1, 1981), pp. 170-186, XP055224968, Retrieved from the Internet: URL:http://tunic.ro/fise/tehnice/05-10020L.pdf * abstract * (1 page).
Colman, et al., "The healing of wounds in the skin of piglets treated with benzoyl peroxide," The Journal of Dermatologic Surgery and Oncology, 4(9):705-707 (1978).
Darzynkiewicz, et al., "Photosensitizing effects of the tricyclic heteroaromatic cationic dyes Pyronin Y and Toluidine Blue O (tolonium chloride)," Cancer Research, 48(5): (6 pages) (1988).
De, et al., "Environmental effects on the aggregation of some xanthene dyes used in lasers," Spectrochimica Acta Part A: Molecular and Biomolecular Spectroscopy, 61(8):1821-1833 (2005).
Decraene et al., "Cellulose acetate containing Toluidine Blue and Rose Bengal is an effective antimicrobial coating when exposed to white light," Applied and Env. Microbiology, 72:6(4436-4439) (Jun. 2006).
European Supplementary Search Report, Application No. EP09824320, dated Mar. 28, 2012 (12 pages).
FDA, Color Additive Status List, http://www.cfsanJda.gov/-dms/opa-appc.html, downloaded Jun. 18, 2008 (13 pages).
FDA, Product Classification Database Search, http://www.accessdata.fda.gov/scripts/cdrh/cfdocs/cfpcd/classificiation/c.f?ID-3964, Device: Eosin y: database, downloaded Jun. 18, 2008 (2 pages).
Fisher Scientific, "Material Safety Data Sheet: Sodium acetate buffer," https://fscimagef.fishersci.com/msds/91502.htm (ACC # 91502) (Apr. 13, 2000) (5 pages).
Goldberg, "Photodynamic therapy in skin rejuvenation," Clinics in Dermatology, 26(6):608-613 (2008).
Jankowski, et al., "The action of photosensitizers and serum in a bactericidal process. II. The effects of dyes: Hypericin, Eosin Y and Saphranine O," Polish Journal of Microbiology, 54(4):323-230 (2005).

Kelly, et al., "Combined photodynamic and photothermal induced injury enhances damage to in vivo model blood vessels," Lasers in Surgery and Medicine, 34(5):407-413 (2004).
Korb, et al, "An evaluation of the efficacy of Fluorescein, Rose Bengal, Lissamine Green, and a new dye mixture for ocular surface staining," Eye Contact Lens, Jan. 2008;34(1) 61-64. Jan. 1, 2008 (Jan. 1, 2008), XP055224976, Retrieved from the Internet: URL:http://www.ncbi.nlm.nih.gov/pubmed/181 80687 [retrieved on Nov. 2, 2015] * abstract * (1 page).
McCullach, et al., "Photosensitized destruction of *Chlorella vulgaris* by Methylene Blue or Nuclear Fast Red combined with hydrogen peroxide under visible light irradiation," Environmental Science and Technology, 40(7):2421-2425 (2006).
Meisel, et al., "Photodynamic therapy for periodontal diseases: state of the art," Journal of Photochemistry and Photobiology B: Biology, 79:159-170 (2005).
Mintel, "Gel Blush," http://gnpd.com; Jun. 2009 (4 pages).
Mintel, "Gold Bear Gums," http://gnpd.com, Feb. 2008 (3 pages).
Mintel, "Teens Braces Cleaner," http://gnpd.com, Jan. 2004 (2 pages).
Mintel, "Velvet Gloss Lip Pencil," http://gnpd.com; Feb. 2011 (4 pages).
Montenegro, et al., "Model studies on the photosensitized isomerization of bixin," Journal of Agriculture and Food Chemistry, 52(2): 367-73 (2004).
Nolan et al., "The efficacy of topical hyaluronic acid in the management of oral lichen planus," Journal of Oral Pathology and Medicine, 38(3):299-303 (2006).
Olympus America Inc., "Special characteristics of common biological stains," http://micro.magnet.fsu.edu/primer/photomicrography/bwstainchart.html, Apr. 30, 2000 (3 pages).
PCT International Preliminary Report on Patentability and Written Opinion for International Serial No. PCT/CA2013/000787, dated Nov. 27, 2013 (9 pages).
PCT International Search Report for International Application No. PCT/CA2010/001134, dated Oct. 8, 2010 (3 pages).
PCT International Search Report and Written Opinion for International Application No. PCT/CA2014/000161, dated May 30, 2014 (12 pages).
PCT International Search Report and Written Opinion for International Application No. PCT/CA2015/000407, dated Sep. 23, 2015 (13 pages).
PCT International Search Report Corrected for International Application No. PCT/CA2014/000261, dated Jul. 23, 2014 (7 pages).
PCT International Search Report for International Application No. PCT/CA2009/001615, dated Feb. 9, 2010 (9 pages).
PCT International Search Report for International Application No. PCT/CA2013/000395, dated Jul. 15, 2013 (12 pages).
PCT International Search Report for International Application No. PCT/CA2014/000536, dated Oct. 16, 2014 (7 pages).
Publication date of following document established by Internet Archive Wayback Machine (3 pages) <URL: <http://web.archive.org/web/20090208211504/http://en.wikipedia.org/wiki/Eosin Aug. 2, 2009.
Resources: Fluorochrome absorption emission wavelengths, [Online] XP002449595 Retrieved from the Internet: URL: http://www.sciencegateway.org/resource s/fae1.htm>[retrieved on Sep. 6, 2007] see p. 2: Rhodamine WT emission nm 555 p. 2 (12 pages).
Roy, et al., "Dermal wound healing is subject to redox control," Molecular Therapy, 13(1):211-220 (2006).
Sezer, et al., "Topical drug delivery using chitosan nano- and microparticles," Expert Opinion in Drug Delivery, Informa UK, 9(9):1129-1146 (2012).
Steinberg, et al., "Genetic and physiological effects of noncoherent visible light combined with hydrogen peroxide on *Streptococcus mutans* in biofilm," Antimicrobial Agents and Chemotherapy, 52(7):2626-2631 (2008).
Subba, et al, "Photocatalytic transformation of dyes and by-products in the presence of hydrogen peroxide," Environmental Technology, 24(8):1025-1030 (2003).
Thompson, et al., "Fluorescence polarization standards for high-throughput screening and imaging," Bio Techniques, 32: (5 pages) (2002).

(56) References Cited

OTHER PUBLICATIONS

Gonzales et al., "Photodynamic inactivation of microorganisms as an innovative approach to kill mucocutaneous and skin microorganisms," Giornale Italiano Di Dermatologia e Venereologia, 145, pp. 477-489 (2010).

Lins, et al., "Enhancement of Antimicrobial Action of Photodynamic Therapy in the Presence of Hydrogen Peroxide, in Microbial Pathogens and Strategies for Combating Them: Science, Technology and Education," Edition: Microbiology Book Series #4, Editor: A. Mendez-Vilas, pp. 367-371 (2013) (acquired from: https://www.researchgate.net/publication/283644315_Enhancement_of_Antimicrobial_Action_of_Photodynamic_Therapy_in_the_Presence_of_Hydrogen_Peroxide).

Mintel, "Active Plus Deep Cleaning Tablets," Database GNPD [Online], [Online], May 2007, XP002769877, Database accession No. 707777 *Ingredients*.

Mintel, "Effervescent Tablets," Database GNPD [Online], May 2009, XP002769876, Database accession No. 1089966 *Ingredients*.

* cited by examiner

CHROMOPHORE COMBINATIONS FOR BIOPHOTONIC USES

This application is a United States National Stage filing under 35 U.S.C. § 371 of International Application No. PCT/CA2013/000786, filed Sep. 13, 2013, which claims the benefit of and is a continuation of U.S. application Ser. No. 13/830,488 filed on Mar. 14, 2013, which application is hereby incorporated by reference in its entirety. PCT/CA2013/000786 also claims priority to U.S. Application 61/701,502 filed on Sep. 14, 2012; U.S. Application 61/701,510 filed on Sep. 14, 2012; U.S. Application 61/701,513 filed on Sep. 14, 2012; U.S. Application 61/766,611 filed on Feb. 19, 2013; U.S. Application 61/873,791 filed on Sep. 4, 2013; PCT Application PCT/CA2013/000395 filed on Apr. 19, 2013; and GB Application 1307157.6 filed on Apr. 19, 2013; which applications are hereby incorporated by reference in their entireties.

BACKGROUND OF THE DISCLOSURE

Phototherapy has recently been recognized as having wide range of applications in both the medical, cosmetic and dental fields for use in surgeries, therapies and examinations. For example, phototherapy has been developed to treat cancers and tumors, to treat skin conditions, to disinfect target sites as an antimicrobial treatment, and to promote wound healing.

Known phototherapy techniques include photodynamic therapy which involves systemic administration or uptake of a photosensitive agent or chromophore into the diseased or injured tissue, followed by site-specific application of activating light. Other types of phototherapy include the use of light alone at specific wavelengths to target tissue using light-emitting diode (LED) or fluorescent lamps, or lasers.

It is an object of the present disclosure to provide new and improved compositions and methods useful in phototherapy.

SUMMARY OF THE DISCLOSURE

The present disclosure provides topical biophotonic compositions and methods of using the biophotonic compositions for the biophotonic treatment of living tissue. Biophotonic treatment may include skin rejuvenation; tissue repair including wound healing, scar removal and scar minimization; treatment of skin conditions such as acne; and treatment of periodontitis.

The biophotonic composition of the present disclosure comprises a gelling agent and at least two xanthene dyes, wherein a first xanthene dye has an emission spectrum that overlaps at least 5%, 10%, 20%, 25%, 30%, 40%, 50%, 60%, 70% with an absorption spectrum of a second xanthene dye. In some embodiments, the first xanthene dye has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second xanthene dye.

Particularly useful combinations of xanthene dyes include but are not limited to: Fluorescein+Eosin Y; Fluorescein+Eosin Y+Rose Bengal; Fluorescein+Eosin Y+Phloxine B; Eosin Y+Rose Bengal; Eosin Y+Phloxine B; Fluorescein+Erythrosine B+Eosin Y; Eosin Y+Erythrosine; Eosin Y+Erythrosine B+Rose Bengal; Eosin Y+Erythrosine B+Phloxine B; Fluorescein+Eosin Y+Erythrosine B+Rose Bengal; and Fluorescein+Eosin Y+Erythrosine B+Phloxine B.

The gelling agent may comprise a hygroscopic substance. In addition or in the alternative, the gelling agent may also be a hydrophilic polymer, a hydrated polymer or a lipid. In certain embodiments, the gelling agent comprises one or more of glycerin, glycols such as propylene glycol, polyacrylic acid polymers, hyaluronic acid, glucosamine sulphate or gelatin.

In certain embodiments, the gelling agent is a high molecular weight, cross-linked polyacrylic acid polymer having a viscosity in the range of about 20,000-80,000, 20,000-100,000, 25,000-90,000, 30,000-80,000, 30,000-70,000, 30,000-60,000, 25,000-40,000 cP. In certain embodiments, the cross-linked polyacrylic acid polymer is a carbomer selected from the group consisting of, but not limited to, Carbopol® 71G NF, 971P NF, 974P NF, 980 NF, 981 NF, 5984 EP, ETD 2020NF, Ultrez 10 NF, 934 NF, 934P NF, 940 NF, 941 NF, or 1342 NF.

In certain embodiments, the biophotonic composition is substantially translucent and/or transparent. In certain embodiment, the biophotonic composition has a translucency of at least 70% at 460 nm. In other embodiments, the composition has a translucency of at least 20%, 30%, 40%, 50%, 60%, 70%, 75%, 85%, 90%, 95% or 100% at 460 nm.

In certain embodiments, the biophotonic composition is a liquid, a gel, a semi-solid, cream, foam, lotion, oil, ointment, paste, suspension, or aerosol spray.

In certain embodiments, the biophotonic composition is encapsulated in a transparent, impermeable membrane, or a breathable membrane which allows permeation of gases but not liquids. The membrane may comprise a lipid.

In certain embodiments, the biophotonic composition further comprises an oxygen-generating agent. In some embodiments, the oxygen-generating agent comprises hydrogen peroxide, carbamide peroxide, benzoyl peroxide, molecular Oxygen or water. When the oxygen-releasing agent is a peroxide, it may be present in values less than 6% $H_2O_2$, from 0.5-6 wt % $H_2O_2$ (or its equivalent), 0.5-5.5%, 0.5-5.0%, 0.5-4.5%, 0.5-4.0%, 0.5-3.5%, 0.5-3.0%, 0.5-2.5%, 0.5-2%, 0.5-1.5%, or 0.5-1.0%.

In certain embodiments, the biophotonic composition does not generate a substantial amount of heat following illumination with light. In some embodiments, the energy emitted by the biophotonic composition does not cause tissue damage.

In certain embodiments, the first and second xanthene dyes are present in the composition in the amount of about 0.001-0.5% per weight of the composition.

In certain embodiments, the biophotonic composition may be applied to or impregnated into a material such as a pad, a dressing, a woven or non-woven fabric or the like. The impregnated material may be used as a mask (e.g. a face mask) or a dressing.

In certain embodiments, the biophotonic composition further comprises at least one waveguide within or adjacent to the composition. The waveguide can be a particle, a fibre or a fibrillar network made of a material which can transmit and/or emit light.

In certain embodiments, the composition does not comprise silica, tanning agents, or non-fluorescent dyes.

The present disclosure also provides uses of the present composition and methods for biophotonic treatment of living tissue.

Accordingly, in some aspects, there is provided a method for providing biophotonic therapy to a wound, comprising: applying to a wound a biophotonic composition comprising at least a first xanthene dye and a second xanthene dye, wherein the first xanthene dye has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second xanthene dye; and illuminating the biophotonic composition with light having a wavelength that overlaps with an absorption spectrum of the first xanthene dye.

In some embodiments of the method for providing biophotonic therapy to a wound, the method promotes wound healing. In certain embodiments of the method, the wound as described herein includes for example chronic or acute wounds, such as diabetic foot ulcers, pressure ulcers, venous ulcers or amputations. In some embodiments of the method for providing biophotonic therapy to a wound, the method promotes reduction of scar tissue formation. In certain embodiments, the treatment can be applied in or on the wound once, twice, three times, four times, five times or six times a week, daily, or at any other frequency. The total treatment time can be one week, two weeks, three weeks, four weeks, five weeks, six weeks, seven weeks, eight weeks, nine weeks, ten weeks, eleven weeks, twelve weeks, or any other length of time deemed appropriate.

In other aspects, there is provided a method for biophotonic treatment of acne comprising: applying to skin tissue a biophotonic composition comprising at least a first xanthene dye and a second xanthene dye, wherein the first xanthene dye has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second xanthene dye; and illuminating the biophotonic composition with light having a wavelength that overlaps with an absorption spectrum of the first xanthene dye. In certain embodiments of the method for biophotonic treatment acne, the treatment can be applied to the skin tissue, such as on the face, once, twice, three times, four times, five times or six times a week, daily, or at any other frequency. The total treatment time can be one week, two weeks, three weeks, four weeks, five weeks, six weeks, seven weeks, eight weeks, nine weeks, ten weeks, eleven weeks, twelve weeks, or any other length of time deemed appropriate. In certain embodiments, the face may be split into separate areas (cheeks, forehead), and each area treated separately. For example, the composition may be applied topically to a first portion, and that portion illuminated with light, and the biophotonic composition then removed. Then the composition is applied to a second portion, illuminated and removed. Finally, the composition is applied to a third portion, illuminated and removed.

The disclosed methods for treating acne or wounds may further include, for example, administering a systemic or topical drug before, during or after the biophotonic treatment. The drug may be an antibiotic, a hormone treatment, or any other pharmaceutical preparation which may help to treat acne or wounds. The combination of a systemic treatment together with a topical biophotonic treatment can reduce the duration of systemic treatment time.

In other aspects, there is provided a method for biophotonic treatment of a skin disorder, comprising: applying to target skin tissue a biophotonic composition comprising at least a first xanthene dye and a second xanthene dye, wherein the first xanthene dye has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second xanthene dye; and illuminating the biophotonic composition with light having a wavelength that overlaps with an absorption spectrum of the first xanthene dye.

In other aspects, there is provided a method for promoting skin rejuvenation, comprising: applying to target skin tissue a biophotonic composition comprising at least a first xanthene dye and a second xanthene dye, wherein the first xanthene dye has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second xanthene dye; and illuminating the biophotonic composition with light having a wavelength that overlaps with an absorption spectrum of the first xanthene dye.

In other aspects, the present disclosure provides a method for treatment of periodontal disease, comprising: applying to a periodontal pocket a biophotonic composition comprising at least a first xanthene dye and a second xanthene dye, wherein the first xanthene dye has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second xanthene dye; and illuminating the biophotonic composition with light having a wavelength that overlaps with an absorption spectrum of the first xanthene dye.

In other aspects, there is provided a method of using a cascade of energy transfer between at least a first and a second fluorescent chromophore to absorb and/or emit light within the visible range of the electromagnetic spectrum for treatment of a skin disorder, treatment of a wound, skin rejuvenation, treatment of periodontitis. The present methods and compositions of the present disclosure may also be used to treat fungal and viral infections.

In certain embodiments of any method of the present disclosure, the biophotonic composition is illuminated for any time period per treatment in which the biophotonic composition is activated, for example 1 to 30 minutes. The distance of the light source from the biophotonic composition can be any distance which can deliver an appropriate light power density to the biophotonic composition and/or the skin tissue, for example 5, 10, 15 or 20 cm. The biophotonic composition is applied topically at any suitable thickness. Typically, the biophotonic composition is applied topically to skin or wounds at a thickness of at least about 2 mm, about 2 mm to about 10 mm.

In certain embodiments, the method of the present disclosure comprises a step of illuminating the biophotonic composition for a period of at least 30 seconds, 2 minutes, 3 minutes, 5 minutes, 7 minutes, 10 minutes, 15 minutes, 20 minutes, 25 minutes, or 30 minutes. In some embodiments, the biophotonic composition is illuminated for a period of at least 3 minutes.

In certain embodiments of the methods of the present disclosure, the biophotonic composition is removed from the site of a treatment following application of light. Accordingly, the biophotonic composition is removed from the site of treatment within at least 30 seconds, 2 minutes, 3 minutes, 5 minutes, 7 minutes, 10 minutes, 15 minutes, 20 minutes, 25 minutes or 30 minutes after application. In some embodiments, the biophotonic composition is illuminated for a period of at least 3 minutes. In some embodiments, the biophotonic composition is removed after a period of at least 3 minutes post application of the biophotonic composition to treatment site.

In certain other embodiments, the biophotonic composition is kept in place for up to one, two or three weeks, and illuminated with light which may include ambient light at various intervals. In this case, the composition may be covered up in between exposure to light. For example, the biophotonic composition may be soaked in a dressing and placed inside or over a wound and be left in place for an extended period of time (e.g. more than one day).

DETAILED DESCRIPTION (1) Overview

Figure 1:
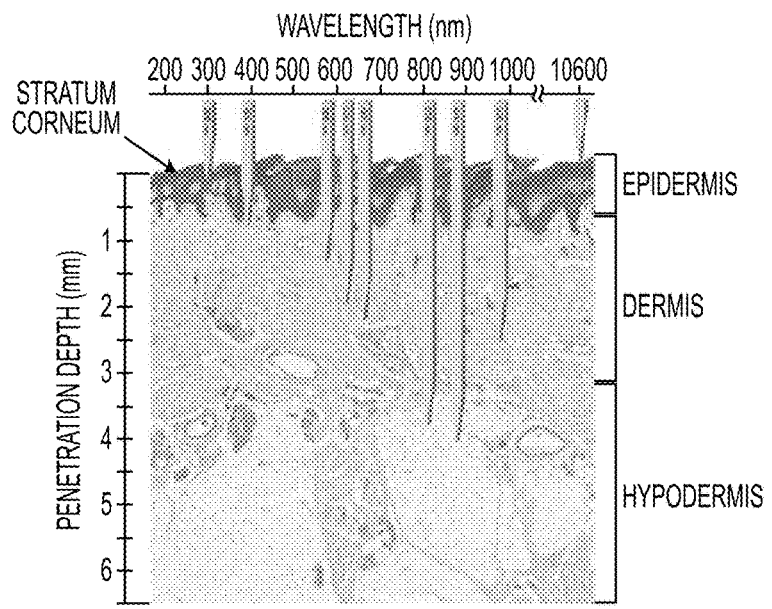
FIG. 1 depicts absorption of light in the various layers of the skin (Samson et al. *Evidence Report/Technology Assessment* 2004, 111, pages 1-97).

The present disclosure provides compositions including at least two photoactive chromophores which can transfer energy from one to the other and methods useful for treating tissue with these compositions for example to promote tissue repair including wound healing, for cosmetic treatment of skin such as for skin rejuvenation, for treating skin disorders such as acne, and for periodontal treatment.

(2) Definitions

Before continuing to describe the present disclosure in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

"Biophotonic" means the generation, manipulation, detection and application of photons in a biologically relevant context. In other words, biophotonic compositions exert their physiological effects primarily due to the generation and manipulation of photons. "Biophotonic composition" is a composition as described herein that may be activated by light to produce photons for biologically relevant applications.

"Topical composition" means a composition to be applied to body surfaces, such as the skin, mucous membranes, vagina, oral cavity, wounds, and the like. A topical composition may be in the form of, including, but not limited to, a cream, gel, ointment, lotion, levigate, solution, bioadhesive, salve, milk. The topical composition may impregnate material such as a pad, sheet, fabric or fibres, dressings, spray, suspension, foam, or the like.

Terms "chromophore", "photoactivating agent" and "photoactivator" are used herein interchangeably. A chromophore means a chemical compound, when contacted by light irradiation, is capable of absorbing the light, for example a xanthene dye. The chromophore readily undergoes photo-excitation and can then transfer its energy to other molecules or emit it as light.

"Oxidant", "oxidizing agent" or "oxygen-releasing agent" which terms are used interchangeably herein, means a chemical compound that readily transfers oxygen atoms and oxidizes other compounds. It includes molecular oxygen as well as oxygen containing compounds such as water, peroxide etc.

"Photobleaching" means the photochemical destruction of a chromophore.

The term "actinic light" is intended to mean light energy emitted from a specific light source (e.g., lamp, LED, or laser) and capable of being absorbed by matter (e.g. the chromophore or photoactivator defined above). In a preferred embodiment, the actinic light is visible light.

"Wound" means an injury to any tissue, including for example, acute, subacute, delayed or difficult to heal wounds, and chronic wounds. Examples of wounds may include both open and closed wounds. Wounds include, for example, burns, incisions, excisions, lesions, lacerations, abrasions, puncture or penetrating wounds, surgical wounds, contusions, hematomas, crushing injuries, ulcers (such as for example pressure, venous, pressure or diabetic), wounds caused by periodontitis (inflammation of the periodontium), and gun-shot wounds.

"Wound healing" means promotion or acceleration of tissue repair including closure of a wound, activation of a chronic wound, or minimizing scar formation.

"Skin rejuvenation" means a process of reducing, diminishing, retarding or reversing one or more signs of skin aging. For instance, common signs of skin aging include, but are not limited to, appearance of fine lines or wrinkles, thin and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, or a blotchy complexion. According to the present disclosure, one or more of the above signs of aging may be reduced, diminished, retarded or even reversed by the compositions and methods of the present disclosure.

(3) Biophotonic Compositions

The present disclosure provides biophotonic compositions. Biophotonic compositions are compositions that, in a broad sense, comprise chromophore(s) which are activated by light and accelerate the dispersion of light energy, which leads to light carrying on a therapeutic effect on its own, and/or to the photochemical activation of other agents contained in the composition (e.g., the break-down of an oxygen-releasing agent when such agent is present in the composition or at the treatment site, leading to the formation of oxygen radicals, such as singlet oxygen). The biophotonic compositions of the present disclosure comprise at least two xanthene dyes as chromophores.

Figure 2:
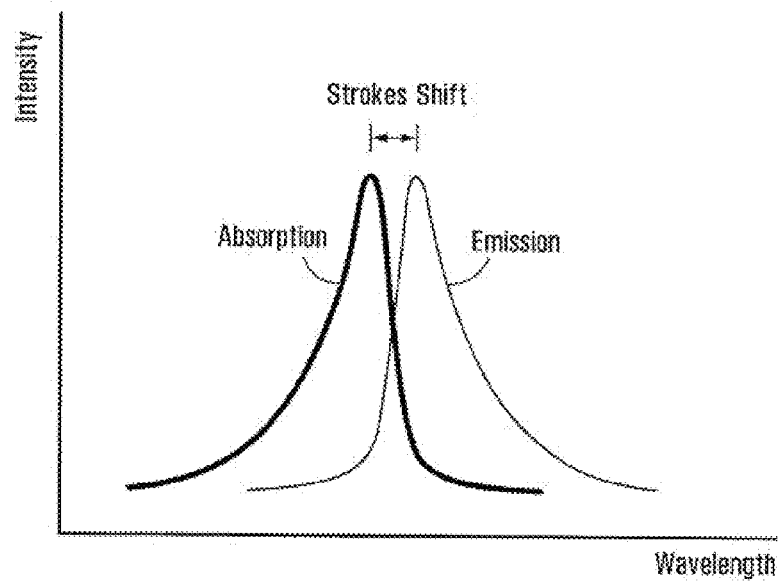
FIG. 2 illustrates the Stokes' shift.

When a chromophore absorbs a photon of a certain wavelength, it becomes excited. This is an unstable condition and the molecule tries to return to the ground state, giving away the excess energy. For some chromophores, it is favorable to emit the excess energy as light when transforming back to the ground state. This process is called fluorescence. The peak wavelength of the emitted fluorescence is shifted towards longer wavelengths compared to the absorption wavelengths due to loss of energy in the conversion process. This is called the Stokes' shift and is illustrated in FIG. 2. In the proper environment (e.g., in a biophotonic composition) much of this energy is transferred to the other components of the composition or to the treatment site directly.

Without being bound to theory, it is thought that fluorescent light emitted by photoactivated chromophores may have therapeutic properties due to its femto-, pico- or nano-second emission properties which may be recognized by biological cells and tissues, leading to favorable biomodulation. Furthermore, the emitted fluorescent light has a longer wavelength and hence a deeper penetration into the tissue than the activating light. Irradiating tissue with such a broad range of wavelengths, including in some embodiments the activating light which passes through the composition, may have different and complementary effects on the cells and tissues. Moreover, the generation of oxygen species (e.g. singlet oxygen) by photoactivated chromophores has been observed by the inventors to cause micro-bubbling within the composition which can have a physical impact on the tissue to which it is applied, for example by dislodging biofilm and debridement of necrotic tissue or providing a pressure stimulation. The biofilm can also be pre-treated with an oxygen-releasing agent to weaken the biofilm before treating with the composition of the present disclosure.

Furthermore, it is thought that use of chromophores in a composition to emit fluorescent light provides the ability to fine-tune the emitted light to a far greater degree than using a light source such as an LED or a laser. For example, according to the therapy or treatment required, chromophores may be chosen according to their emitted light wavelength, and appropriate concentrations used to control the power density of the emitted light.

The biophotonic compositions of the present disclosure are substantially transparent/translucent and/or have high light transmittance in order to permit light dissipation into and through the composition. In this way, the area of tissue under the composition can be treated both with the fluorescent light emitted by the composition and the light irradiating the composition to activate it. The % transmittance of the biophotonic composition can be measured in the range of wavelengths from 250 nm to 800 nm using, for example, a Perkin-Elmer Lambda 9500 series UV-visible spectrophotometer. In some embodiments, transmittance of the compositions disclosed herein is measured at 460 nm.

As transmittance is dependent upon thickness, the thickness of each sample can be measured with calipers prior to loading in the spectrophotometer. Transmittance values can be normalized to a thickness of 100 μm (or any thickness) according to:

$$F_{T-corr}(\lambda, t_2) = [e^{-\sigma_t(\lambda)t_1}]^{\frac{t_2}{t_1}} = [F_{T-corr}(\lambda, t_1)]^{\frac{t_2}{t_1}},$$

where, $t_1$=actual specimen thickness, $t_2$=thickness to which transmittance measurements can be normalized.

In some embodiments, the biophotonic composition has a transparency or translucency that exceeds 15%, 20%, 30%, 40%, 50%, 55%, 60%, 65%, 70%, 75%, 80%, or 85% at 460 nm. In some embodiments, the transparency exceeds 70% at 460 nm, 86% at 460 nm, 87% at 460 nm, 88% at 460 nm, 89% at 460 nm, 90% at 460 nm, 91% at 460 nm, 92% at 460 nm, 93% at 460 nm, 94% at 460 nm, 95% at 460 nm, 96% at 460 nm, 97% at 460 nm, 98% at 460 nm or 99% at 460 nm.

The biophotonic compositions of the present disclosure are for topical uses. These compositions may be described based on the components making up the composition. Additionally or alternatively, the compositions of the present disclosure have functional and structural properties and these properties may also be used to define and describe the compositions. Individual components of the composition of the present disclosure are detailed as below.

(a) Chromophores

The biophotonic topical compositions of the present disclosure comprise at least two xanthene dyes as the chromophores. Combining xanthene dyes may increase photoabsorption by the combined dye molecules and enhance absorption and photobiomodulation selectivity. This creates multiple possibilities of generating new photosensitive, and/or selective xanthene dye mixtures.

Figure 3:
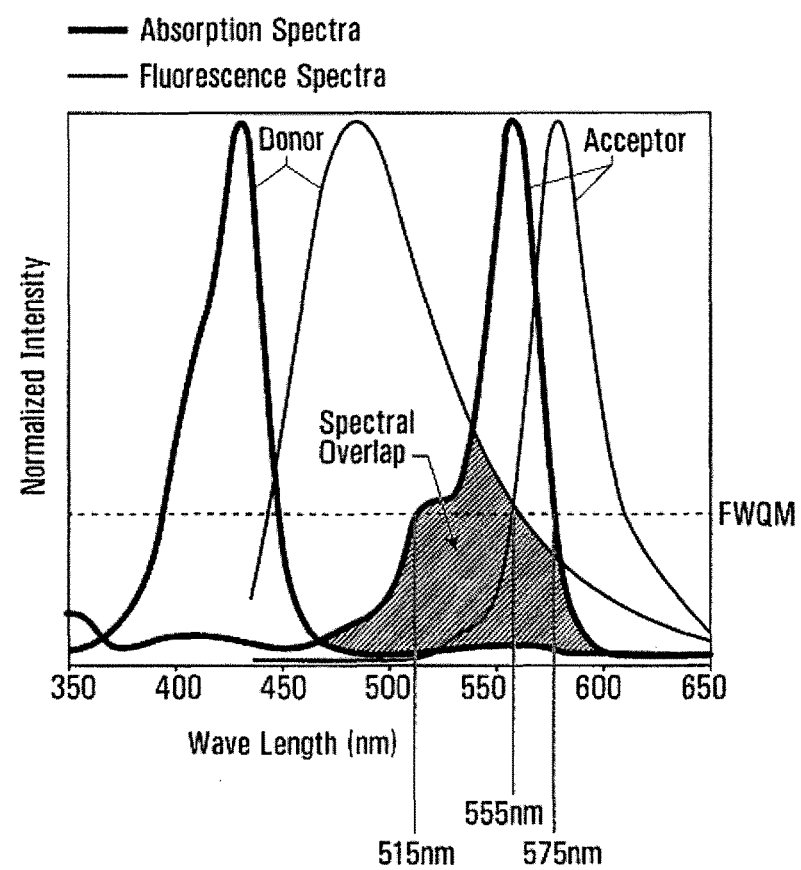
FIG. 3 illustrates the absorption and emission spectra of donor and acceptor chromophores. The spectral overlap between the absorption spectrum of the acceptor chromophore and the emission spectrum of the donor chromophore is also shown.

When such multi-xanthene dye compositions are illuminated with light of an appropriate wavelength to activate at least one of the xanthene dyes, energy transfer can occur between the xanthene dyes. This process, known as resonance energy transfer, is a photophysical process through which an excited 'donor' xanthene dye (also referred to herein as first xanthene dye) transfers its excitation energy to an 'acceptor' xanthene dye (also referred to herein as second xanthene dye). The efficiency and directedness of resonance energy transfer depends on the spectral features of donor and acceptor xanthene dyes. In particular, the flow of energy between xanthene dyes is dependent on a spectral overlap reflecting the relative positioning and shapes of the absorption and emission spectra. For energy transfer to occur the emission spectrum of the donor xanthene dye must preferably overlap with the absorption spectrum of the acceptor xanthene dye (FIG. 3).

Figure 4:
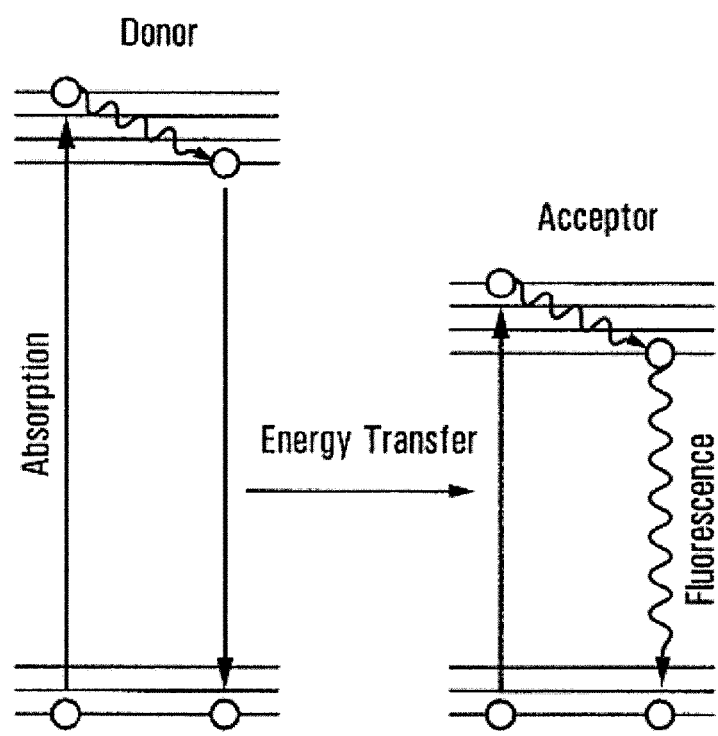
FIG. 4 is a schematic of a Jablonski diagram that illustrates the coupled transitions involved between a donor emission and acceptor absorbance.

Energy transfer manifests itself through decrease or quenching of the donor emission and a reduction of excited state lifetime accompanied also by an increase in acceptor emission intensity. FIG. 4 is a Jablonski diagram that illustrates the coupled transitions involved between a donor emission and acceptor absorbance.

To enhance the energy transfer efficiency, the donor xanthene dye should have good abilities to absorb photons and emit photons. Furthermore, it is thought that the more overlap there is between the donor xanthene dye's emission spectra and the acceptor xanthene dye's absorption spectra, the better a donor xanthene dye can transfer energy to the acceptor xanthene dye.

In some embodiments, the first xanthene dye has an emission spectrum that overlaps at least about 80%, 50%, 40%, 30%, 20%, 10% with an absorption spectrum of the xanthene dye chromophore. In one embodiment, the first xanthene dye has an emission spectrum that overlaps at least about 20% with an absorption spectrum of the second xanthene dye. In some embodiments, the first xanthene dye has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second xanthene dye.

% spectral overlap, as used herein, means the % overlap of a donor xanthene dye's emission wavelength range with an acceptor xanthene dye's absorption wavelength rage, measured at spectral full width quarter maximum (FWQM). For example, FIG. 3 shows the normalized absorption and emission spectra of donor and acceptor xanthene dyes. The spectral FWQM of the acceptor xanthene dye's absorption spectrum is from about 60 nm (515 nm to about 575 nm). The overlap of the donor xanthene dye's spectrum with the absorption spectrum of the acceptor xanthene dye is about 40 nm (from 515 nm to about 555 nm). Thus, the % overlap can be calculated as 40 nm/60 nm×100=66.6%.

In some embodiments, the second xanthene dye absorbs at a wavelength in the range of the visible spectrum. In certain embodiments, the second xanthene dye has an absorption wavelength that is relatively longer than that of the first xanthene dye within the range of about 50-250, 25-150 or 10-100 nm.

As discussed above, the application of light to the compositions of the present disclosure can result in a cascade of energy transfer between the xanthene dyes. In certain embodiments, such a cascade of energy transfer provides photons that penetrate the epidermis, dermis and/or mucosa at the target tissue, including, such as, a site of wound, or a tissue afflicted with acne or another skin disorder. In some embodiments, such a cascade of energy transfer is not accompanied by concomitant generation of heat. In some other embodiments, the cascade of energy transfer does not result in tissue damage.

In some embodiments, the first xanthene dye absorbs at a wavelength in the range of the visible spectrum, such as at a wavelength of about 380-800 nm, 380-700, or 380-600 nm. In other embodiments, the first xanthene dye absorbs at a wavelength of about 200-800 nm, 200-700 nm, 200-600 nm or 200-500 nm. In one embodiment, the first xanthene dye absorbs at a wavelength of about 200-600 nm. In some embodiments, the first xanthene dye absorbs light at a wavelength of about 200-300 nm, 250-350 nm, 300-400 nm, 350-450 nm, 400-500 nm, 400-600 nm, 450-650 nm, 600-700 nm, 650-750 nm or 700-800 nm.

It will be appreciated by those skilled in the art that optical properties of a particular xanthene dye may vary depending on the xanthene dye's surrounding medium. Therefore, as used herein, a particular xanthene dye's absorption and/or emission wavelength (or spectrum) corresponds to the wavelengths (or spectrum) measured in a biophotonic composition of the present disclosure.

Exemplary xanthene dyes include but are not limited to Eosin B (4',5'-dibromo,2',7'-dinitr-o-fluorescein, dianion); eosin Y; eosin Y (2',4',5',7'-tetrabromo-fluoresc-ein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachlor-o-fluorescein, dianion); eosin; eosin dicetylpyridinium chloride ion pair; erythrosin B (2',4',5',7'-tetraiodo-fluorescein, dianion); erythrosin; erythrosin dianion; erythiosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodo-fluorescein, dianion); pyronin G, pyronin J, pyronin Y; Rhodamine dyes such as rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

In certain embodiments, the first xanthene dye is present in an amount of about 0.01-40% per weight of the composition, and the second xanthene dye is present in an amount of about 0.001-40% per weight of the composition. In certain embodiments, the total weight per weight of xanthene dyes is in the amount of about 0.01-40.001% per weight of the composition. In certain embodiments, the first xanthene dye is present in an amount of about 0.01-1%, 0.01-2%, 0.05-1%, 0.05-2%, 1-5%, 2.5-7.5%, 5-10%, 7.5-

12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the second xanthene dye is present in an amount of about 0.001-1%, 0.001-2%, 0.001-0.01%, 0.01-0.1%, 0.1-1.0%, 1-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the total weight per weight of xanthene dyes is in the amount of about less than 0.5%, less than 0.1%, 0.001-0.1%, 0.01-1%, 0.01-2%, 0.05-2%, 0.001-0.5%, 0.5-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.05% per weight of the composition. All amounts are given as weight percentages per weight of the total concentration, and the equivalent weight or volume amounts.

In certain embodiments, the ratio of the concentrations of the first and second xanthene dyes in the composition range from 1:1 to 1:1000. In certain embodiments, the relative concentration of Eosin Y: Fluorescein may be such that there is less Eosin Y than Fluorescein such as 1000:1 or 100:1 or 10:1 or 60-80%: 20-40%. In certain embodiments, the ratio of Eosin Y to Rose Bengal is 1:1 or 70-90%:10-30%. In certain embodiments, the ratio of Fluorescein to Eosin Y to Rose Bengal can be 20-40%: 30-60%: 10-20%. The ratio can be tailored according to the emitted light spectrum desired for a given treatment or therapy.

In some embodiments, the xanthene dye combinations are selected such that their emitted fluorescent light, on photoactivation, is within one or more of the green, yellow, orange, red and infrared portions of the electromagnetic spectrum, for example having a peak wavelength within the range of about 490 nm to about 800 nm. In certain embodiments, the emitted fluorescent light has a power density of between 0.005 to about 10 mW/cm$^2$, about 0.5 to about 5 mW/cm$^2$, or about 0.05 to about 2 mW/cm$^2$.

Particularly useful combinations of xanthene dyes include but are not limited to: Fluorescein+Eosin Y; Fluorescein+Eosin Y+Rose Bengal; Fluorescein+Eosin Y+Phloxine B; Eosin Y+Rose Bengal; Eosin Y+Phloxine B; Eosin Y+Erythrosine; Fluorescein+Erythrosine B+Eosin Y; Eosin Y+Erythrosine B+Rose Bengal; Eosin Y+Erythrosine B+Phloxine B; Fluorescein+Eosin Y+Erythrosine B+Rose Bengal; and Fluorescein+Eosin Y+Erythrosine B+Phloxine B.

It is thought that at least some of these combinations have a synergistic effect at certain concentration ratios within the composition. For example, at certain concentration ratios and with an appropriate activating light, Eosin Y can transfer energy to Rose Bengal, Erythrosin B or Phloxine B when activated. This transferred energy is then emitted as fluorescence and/or by production of reactive oxygen species (such as singlet oxygen).

The synergistic effect may be apparent by the composition having a light absorption spectrum which spans a broader range of wavelengths compared to an individual light absorption spectrum of one of the individual chromophores in the composition, when the individual chromophores and the composition are activated by the same activating light (light having substantially the same emission spectra). This may confer on the composition the ability to be activated by a broader range of activating light wavelengths, for example by white light avoiding the need for a precise wavelength of activating light.

The synergistic effect may also be evident through the composition having a light emission spectrum which spans a broader range of wavelengths compared to an individual light absorption spectrum of one of the individual chromophores in the composition, when the individual chromophores and the composition are activated by the same activating light. This absorbed and re-emitted light spectrum is thought to be transmitted throughout the composition, and also to be transmitted into the site of treatment. This emitted spectrum will then illuminate the target tissue with different penetration depths (FIG. 1), which may confer on the target tissue beneficial therapeutic effects. For example green light has been reported to have wound healing properties. By emitting a broader range of wavelengths, a broader range of therapeutic effects can be achieved. The emitted wavelength can be fine-tuned using different chromophore combinations and concentrations.

The synergistic effect may also be evident through the composition having a higher light absorption or emission peak compared to an individual light absorption/emission peak of one of the individual chromophores in the composition, when the individual chromophores and the composition are activated by the same activating light. The ability to absorb and emit higher levels of photons may have a therapeutic effect in certain applications. Furthermore, less concentration of an individual chromophore may be required to achieve a certain power density. Higher power densities can equate to shorter treatment times.

The synergistic effect may also be evident through the composition producing more oxygen species, in the presence of an oxygen-releasing agent, compared to oxygen species produced by an individual chromophores in the composition, when the individual chromophores and the composition are activated by the same activating light. The ability to produce higher levels of oxygen species without the need to extend treatment time or increase the power density of the activating light may be advantageous in certain situations.

By means of synergistic effects of the xanthene dye combinations in the composition, xanthene dyes which cannot normally be activated by an activating light (such as a blue light) can be activated through energy transfer from xanthene dyes which are activated by the activating light. In this way, the different properties of photoactivated xanthene dyes can be harnessed and tailored according to the cosmetic or the medical therapy required.

For example, Rose Bengal can generate a high yield of singlet oxygen when photoactivated in the presence of molecular oxygen, however it has a low quantum yield in terms of emitted fluorescent light. Rose Bengal has a peak absorption around 540 nm and so is normally activated by green light. Eosin Y has a high fluorescence quantum yield and can be activated by blue light. By combining Rose Bengal with Eosin Y, one obtains a composition which can emit therapeutic fluorescent light and generate singlet oxygen when activated by blue light. In this case, the blue light is thought to photoactivate Eosin Y which transfers some of its energy to Rose Bengal as well as emitting some energy as fluorescence.

One or more of the chromophores may photobleach during illumination. This can be a visible confirmation of 'dose' delivery. As the chromophores photobleach, they emit less fluorescence over time. At the same time, they also absorb less of the activating light over time and so the tissues receive increasingly higher amounts of the activating light.

In this way, the chromophores modulate exposure of the tissue to the light which may provide a somewhat protective effect.

(b) Additional Chromophores

In addition to the xanthene dye combination, the biophotonic topical compositions of the present disclosure may also include, but are not limited to the following:

Chlorophyll Dyes

Exemplary chlorophyll dyes include but are not limited to chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Methylene Blue Dyes

Exemplary methylene blue derivatives include but are not limited to 1-methyl methylene blue; 1,9-dimethyl methylene blue; methylene blue; methylene blue (16 .mu.M); methylene blue (14 .mu.M); methylene violet; bromomethylene violet; 4-iodomethylene violet; 1,9-dimethyl-3-dimethyl-amino-7-diethyl-a-mino-phenothiazine; and 1,9-dimethyl-3-diethylamino-7-dibutyl-amino-phenot-hiazine.

Azo Dyes

Exemplary azo (or diazo-) dyes include but are not limited to methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

In some aspects of the disclosure, the additional chromophores of the biophotonic composition disclosed herein can be independently selected from any of Acid black 1, Acid blue 22, Acid blue 93, Acid fuchsin, Acid green, Acid green 1, Acid green 5, Acid magenta, Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin, Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine O, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2 (Saffranin O), Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid (acid red 4), Celestine blue B, China blue, Cochineal, Coelestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, DiOC6, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Imperial red, Indocyanin green, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta O, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red O, Orange G, Orcein, Pararosanilin, Phloxine B, phycobilins, Phycocyanins, Phycoerythrins. Phycoerythrincyanin (PEC), Phthalocyanines, Picric acid, Ponceau 2R, Ponceau 6R, Ponceau B, Ponceau de Xylidine, Ponceau S, Primula, Purpurin, Pyronin B, Pyronin G, Pyronin Y, Rhodamine B, Rosanilin, Rose bengal, Saffron, Safranin O, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow S, Swiss blue, Tartrazine, Thioflavine S, Thioflavine T, Thionin, Toluidine blue, Toluyline red, Tropaeolin G, Trypaflavine, Trypan blue, Uranin, Victoria blue 4R, Victoria blue B, Victoria green B, Water blue I, Water soluble eosin, Xylidine ponceau, or Yellowish eosin.

In certain embodiments, the composition of the present disclosure includes any of the additional chromophores listed above in addition to the xanthene dyes, or a combination thereof, so as to provide a biophotonic impact at the application site. This is a distinct application of these agents and differs from the use of chromophores as simple stains or as a catalyst for photo-polymerization.

Chromophores can be selected, for example, on their emission wavelength properties in the case of fluorophores, on the basis of their energy transfer potential, their ability to generate reactive oxygen species, or their antimicrobial effect. These needs may vary depending on the condition requiring treatment. For example, chlorophylls may have an antimicrobial effect on bacteria found on the face.

(c) Gelling Agent

The composition may optionally comprise a gelling agent. A gelling agent for use according to the present disclosure may comprise any ingredient suitable for use in a topical biophotonic formulation as described herein. The gelling agent may be an agent capable of forming a cross-linked matrix, including physical and/or chemical cross-links. The gelling agent is preferably biocompatible, and may be biodegradable. In some embodiments, the gelling agent is able to form a hydrogel or a hydrocolloid. An appropriate gelling agent is one that can form a viscous liquid or a semisolid. In preferred embodiments, the gelling agent and/or the composition has appropriate light transmission properties. It is also important to select a gelling agent which will allow biophotonic activity of the chromophores. For example, some chromophores require a hydrated environment in order to fluoresce. The gelling agent may be able to form a gel by itself or in combination with other ingredients such as water or another gelling agent, or when applied to a treatment site, or when illuminated with light.

In some embodiments the composition is in the form of a gel, cream, ointment, lotion, paste, spray or foam.

The gelling agent according to various embodiments of the present disclosure may comprise polyalkylene oxides, particularly polyethylene glycol and poly(ethylene oxide)-poly(propylene oxide) copolymers, including block and random copolymers; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxy-ethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropyl-acrylamide); poly(olefinic alcohol)s such as poly(vinyl alcohol); poly(N-vinyl lactams) such as poly(vinyl pyrrolidone), poly(N-vinyl caprolactam), and copolymers thereof, polyoxazolines, including poly(methyloxazoline) and poly(ethyloxazoline); and polyvinylamines.

The gelling agent according to certain embodiments of the present disclosure may comprise a polymer selected from any of synthetic or semi-synthetic polymeric materials, polyacrylate copolymers, cellulose derivatives and polymethyl vinyl ether/maleic anhydride copolymers. In some embodiments, the hydrophilic polymer comprises a polymer that is a high molecular weight (i.e., molar masses of more than about 5,000, and in some instances, more than about 10,000, or 100,000, or 1,000,000) and/or cross-linked polyacrylic acid polymer. In some embodiments, the polymer is a polyacrylic acid polymer and has a viscosity in the range of about 15,000-100,000, 15,000-90,000, 15,000-80,000, 20,000-80,000, 20,000-70,000, 20,000-40,000 cP. In certain embodiment, the polymer is a high molecular weight, and/or cross-linked polyacrylic acid polymer, where the polyacrylic acid polymer has a viscosity in the range of about 15,000-80,000 cP.

Carbomers may be used. Carbomers are synthetic high molecular weight polymer of acrylic acid that are cross-linked with either allylsucrose or allylethers of pentaerythritol having a molecular weight of about $3 \times 10^6$. The gelation mechanism depends on neutralization of the carboxylic acid moiety to form a soluble salt. The polymer is hydrophilic and produces sparkling clear gels when neutralized. Carbomer gels possess good thermal stability in that gel viscosity and yield value are essentially unaffected by temperature. As a topical product, carbomer gels possess optimum rheological properties. The inherent pseudoplastic flow permits immediate recovery of viscosity when shear is terminated and the high yield value and quick break make it ideal for dispensing. Aqueous solution of Carbopol® is acidic in nature due to the presence of free carboxylic acid residues. Neutralization of this solution cross-links and gelatinizes the polymer to form a viscous integral structure of desired viscosity.

Carbomers are available as fine white powders which disperse in water to form acidic colloidal suspensions (a 1% dispersion has approx. pH 3) of low viscosity. Neutralization of these suspensions using a base, for example sodium, potassium or ammonium hydroxides, low molecular weight amines and alkanolamines, results in the formation of translucent gels. Nicotine salts such as nicotine chloride form stable water-soluble complexes with carbomers at about pH 3.5 and are stabilized at an optimal pH of about 5.6.

In some embodiments of the disclosure, the carbomer is Carbopol. Such polymers are commercially available from B.F. Goodrich or Lubrizol under the designation Carbopol® 71G NF, 420, 430, 475, 488, 493, 910, 934, 934P, 940, 971PNF, 974P NF, 980 NF, 981 NF and the like. Carbopols are versatile controlled-release polymers, as described by Brock (Pharmacotherapy, 14:430-7 (1994)) and Durrani (Pharmaceutical Res. (Supp.) 8:S-135 (1991)), and belong to a family of carbomers which are synthetic, high molecular weight, non-linear polymers of acrylic acid, crosslinked with polyalkenyl polyether. In some embodiments, the carbomer is Carbopol® 974P NF, 980 NF, 5984 EP, ETD 2020NF, Ultrez 10 NF, 934 NF, 934P NF or 940 NF. In certain embodiments, the carbomer is Carbopol® 980 NF, ETD 2020 NF, Ultrez 10 NF, Ultrez 21 or 1382 Polymer, 1342 NF, 940 NF.

In certain embodiments, the gelling agent comprises a hygroscopic material. By hygroscopic material is meant a substance capable of taking up water, for example, by absorption or adsorption even at relative humidity as low as 50%, at room temperature (e.g. about 25° C.). The hygroscopic material may include, but is not limited to, glucosamine, glycosaminoglycan, poly(vinyl alcohol), poly(2-hydroxyethylmethylacrylate), polyethylene oxide, collagen, chitosan, alginate, a poly(acrylonitrile)-based hydrogel, poly(ethylene glycol)/poly(acrylic acid) interpenetrating polymer network hydrogel, polyethylene oxide-polybutylene terephthalate, hyaluronic acid, high-molecular-weight polyacrylic acid, poly(hydroxy ethylmethacrylate), poly(ethylene glycol), tetraethylene glycol diacrylate, polyethylene glycol methacrylate, and poly(methyl acrylate-co-hydroxyethyl acrylate).

The biophotonic composition of the present disclosure may be further encapsulated, e.g, in a membrane. Such a membrane may be transparent, and/or substantially, or fully impermeable. The membrane may be impermeable to liquid but permeable to gases such as air. In certain embodiments, the composition may form a membrane that encapsulates the chromophore(s) of the biophotonic topical composition, where the membrane may be substantially impermeable to liquid and/or gas.

The composition may include any other carrier.

(d) Oxygen-releasing Agents

According to certain embodiments, the compositions of the present disclosure may optionally further comprise an oxygen-releasing agent, for example, as a source of oxygen.

When a biophotonic composition of the present disclosure comprising an oxygen-releasing agent is illuminated with light, the xanthene dyes are excited to a higher energy state. When the xanthene dyes' electrons return to a lower energy state, they emit photons with a lower energy level, thus causing the emission of light of a longer wavelength (Stokes' shift). In the proper environment, some of this energy release is transferred to oxygen or the reactive hydrogen peroxide and causes the formation of oxygen radicals, such as singlet oxygen. The singlet oxygen and other reactive oxygen species generated by the activation of the biophotonic composition are thought to operate in a hormetic fashion. That is, a health beneficial effect that is brought about by the low exposure to a normally toxic stimuli (e.g. reactive oxygen), by stimulating and modulating stress response pathways in cells of the targeted tissues. Endogenous response to exogenous generated free radicals (reactive oxygen species) is modulated in increased defense capacity against the exogenous free radicals and induces acceleration of healing and regenerative processes. Furthermore, activation of the composition can also produce an antibacterial effect. The extreme sensitivity of bacteria to exposure to free radicals makes the composition of the present disclosure a de facto bactericidal composition.

As stated above, the generation of oxygen species by the composition in some embodiments is accompanied by the micro-bubbling which can contribute to debridement or dislodging of biofilm at the site of application. This can allow for the improved penetration of the activating and/or fluorescence light to the treatment site for example to deactivate bacterial colonies leading to their reduction in number.

Suitable oxygen-releasing agents that may be included in the composition include, but are not limited to peroxides such as hydrogen peroxide, urea hydrogen peroxide and benzoyl peroxide. Peroxide compounds are oxygen-releasing agents that contain the peroxy group (R—O—O—R), which is a chainlike structure containing two oxygen atoms, each of which is bonded to the other and a radical or some element.

Hydrogen peroxide ($H_2O_2$) is the starting material to prepare organic peroxides. $H_2O_2$ is a powerful oxygen-releasing agent, and the unique property of hydrogen peroxide is that it breaks down into water and oxygen and does not form any persistent, toxic residual compound. Hydrogen peroxide for use in this composition can be used in a gel, for example with 6% hydrogen peroxide. A suitable range of concentration over which hydrogen peroxide can be used in the present composition is from about 0.1% to about 6%.

Urea hydrogen peroxide (also known as urea peroxide, carbamide peroxide or percarbamide) is soluble in water and contains approximately 35% hydrogen peroxide. Carbamide peroxide for use in this composition can be used as a gel, for example with 16% carbamide peroxide that represents 5.6% hydrogen peroxide, or 12% carbamide peroxide. A suitable range of concentration over which urea peroxide can be used in the present composition is from about 0.3% to about 16%. Urea hydrogen peroxide breaks down to urea and hydrogen peroxide in a slow-release fashion that can be accelerated with heat or photochemical reactions. The released urea [carbamide, $(NH_2)CO_2)$], is highly soluble in water and is a powerful protein denaturant. It increases solubility of some proteins and enhances rehydration of the skin and/or mucosa.

Benzoyl peroxide consists of two benzoyl groups (benzoic acid with the H of the carboxylic acid removed) joined by a peroxide group. It is found in treatments for acne, in concentrations varying from 2.5% to 10%. The released peroxide groups are effective at killing bacteria. Benzoyl peroxide also promotes skin turnover and clearing of pores, which further contributes to decreasing bacterial counts and reduce acne. Benzoyl peroxide breaks down to benzoic acid and oxygen upon contact with skin, neither of which is toxic. A suitable range of concentration over which benzoyl peroxide can be used in the present composition is from about 2.5% to about 5%.

Other oxygen-releasing agents include molecular oxygen, water, perbonates and carbonates. Oxygen-releasing agents can be provided in powder, liquid or gel form within the composition. The composition may include an amount of oxygen-releasing agent, which is augmented by the separate application of oxygen-releasing agents to the treatment site. Alternatively, oxygen-releasing agents may also be applied to the tissue site separately to the composition.

(e) Healing Factors

The composition of the present disclosure may comprise healing factors. Healing factors comprise compounds that promote or enhance the healing or regenerative process of the tissues on the application site of the composition. During the photoactivation of the composition of the present disclosure, there is an increase of the absorption of molecules at the treatment site by the skin, wound or the mucosa. An augmentation in the blood flow at the site of treatment is observed for an extent period of time. An increase in the lymphatic drainage and a possible change in the osmotic equilibrium due to the dynamic interaction of the free radical cascades can be enhanced or even fortified with the inclusion of healing factors. Suitable healing factors include, but are not limited to:

Hyaluronic acid (Hyaluronan, hyaluronate): is a non-sulfated glycosaminoglycan, distributed widely throughout connective, epithelial and neural tissues. It is one of the primary components of the extracellular matrix, and contributes significantly to cell proliferation and migration. Hyaluronan is a major component of the skin, where it is involved in tissue repair. While it is abundant in extracellular matrices, it contributes to tissues hydrodynamics, movement and proliferation of cells and participates in a wide number of cell surface receptor interactions, notably those including primary receptor CD44. The hyaluronidases enzymes degrade hyaluronan. There are at least seven types of hyaluronidase-like enzymes in humans, several of which are tumor suppressors. The degradation products of hyaluronic acid, the oligosaccharides and the very-low molecular weight hyaluronic acid, exhibit pro-angiogenic properties. In addition, recent studies show that hyaluronan fragments, but not the native high molecular mass of hyaluronan, can induce inflammatory responses in macrophages and dendritic cells in tissue injury. Hyaluronic acid is well suited to biological applications targeting the skin. Due to its high biocompatibility, it is used to stimulate tissue regeneration. Studies have shown hyaluronic acid appearing in the early stages of healing to physically create room for white blood cells that mediate the immune response. It is used in the synthesis of biological scaffolds for wound healing applications and in wrinkle treatment. A suitable range of concentration over which hyaluronic acid can be used in the present composition is from about 0.001% to about 3%.

Glucosamine: is one of the most abundant monosaccharides in human tissues and a precursor in the biological synthesis of glycosilated proteins and lipids. It is commonly used in the treatment of osteoarthritis. The common form of glucosamine used is its sulfate salt. Glucosamine shows a number of effects including an anti-inflammatory activity, stimulation of the synthesis of proteoglycans and the synthesis of proteolytic enzymes. A suitable range of concentration over which glucosamine can be used in the present composition is from about 0.01% to about 3%.

Allantoin: is a diureide of glyosilic acid. It has keratolytic effect, increases the water content of the extracellular matrix, enhances the desquamation of the upper layers of dead (apoptotic) skin cells, and promotes skin proliferation and wound healing.

(f) Antimicrobials

The composition of the present disclosure may comprise antimicrobial agents. Antimicrobials kill microbes or inhibit their growth or accumulation. Exemplary antimicrobials (or antimicrobial agent) are recited in U.S. Patent Application Publications 20040009227 and 20110081530. Suitable antimicrobials for use in the methods of the present disclosure include, but not limited to, phenolic and chlorinated phenolic and chlorinated phenolic compounds, resorcinol and its derivatives, bisphenolic compounds, benzoic esters (parabens), halogenated carbonilides, polymeric antimicrobial agents, thazolines, trichloromethylthioimides, natural antimicrobial agents (also referred to as "natural essential oils"), metal salts, and broad-spectrum antibiotics.

Specific phenolic and chlorinated phenolic antimicrobial agents that can be used in the disclosure include, but are not limited to: phenol; 2-methyl phenol; 3-methyl phenol; 4-methyl phenol; 4-ethyl phenol; 2,4-dimethyl phenol; 2,5-dimethyl phenol; 3,4-dimethyl phenol; 2,6-dimethyl phenol; 4-n-propyl phenol; 4-n-butyl phenol; 4-n-amyl phenol; 4-tert-amyl phenol; 4-n-hexyl phenol; 4-n-heptyl phenol; mono- and poly-alkyl and aromatic halophenols; p-chlorophenyl; methyl p-chlorophenol; ethyl p-chlorophenol; n-propyl p-chlorophenol; n-butyl p-chlorophenol; n-amyl p-chlorophenol; sec-amyl p-chlorophenol; n-hexyl p-chlorophenol; cyclohexyl p-chlorophenol; n-heptyl p-chlorophenol; n-octyl; p-chlorophenol; o-chlorophenol; methyl o-chlorophenol; ethyl o-chlorophenol; n-propyl o-chlorophenol; n-butyl o-chlorophenol; n-amyl o-chlorophenol; tert-amyl o-chlorophenol; n-hexyl o-chlorophenol; n-heptyl o-chlorophenol; o-benzyl p-chlorophenol; o-benxyl-m-methyl p-chlorophenol; o-benzyl-m,m-dimethyl p-chlorophenol; o-phenylethyl p-chlorophenol; o-phenylethyl-m-methyl p-chlorophenol; 3-methyl p-chlorophenol 3,5-dimethyl p-chlorophenol, 6-ethyl-3-methyl p-chlorophenol, 6-n-propyl-3-methyl p-chlorophenol; 6-iso-propyl-3-methyl p-chlorophenol; 2-ethyl-3,5-dimethyl p-chlorophenol; 6-sec-butyl-3-methyl p-chlorophenol; 2-iso-propyl-3,5-dimethyl p-chlorophenol; 6-diethylmethyl-3-methyl p-chlorophenol; 6-iso-propyl-2-ethyl-3-methyl p-chlorophenol; 2-sec-amyl-3,5-dimethyl p-chlorophenol; 2-diethylmethyl-3,5-dimethyl p-chlorophenol; 6-sec-octyl-3-methyl p-chlorophenol; p-chloro-m-cresol p-bromophenol; methyl p-bromophenol; ethyl p-bromophenol; n-propyl p-bromophenol; n-butyl p-bromophenol; n-amyl p-bromophenol; sec-amyl p-bromophenol; n-hexyl p-bromophenol; cyclohexyl p-bromophenol; o-bromophenol; tert-amyl o-bromophenol; n-hexyl o-bromophenol; n-propyl-m,m-dimethyl o-bromophenol; 2-phenyl phenol; 4-chloro-2-methyl phenol; 4-chloro-3-methyl phenol; 4-chloro-3,5-dimethyl phenol; 2,4-dichloro-3,5-dimethylphenol; 3,4,5,6-tetabromo-2-methylphenol-; 5-methyl-2-pentylphenol; 4-isopropyl-3-methylphenol; para-chloro-metaxylenol (PCMX); chlorothymol; phenoxyethanol; phenoxyisopropanol; and 5-chloro-2-hydroxydiphenylmethane.

Resorcinol and its derivatives can also be used as antimicrobial agents. Specific resorcinol derivatives include, but are not limited to: methyl resorcinol; ethyl resorcinol; n-propyl resorcinol; n-butyl resorcinol; n-amyl resorcinol; n-hexyl resorcinol; n-heptyl resorcinol; n-octyl resorcinol; n-nonyl resorcinol; phenyl resorcinol; benzyl resorcinol; phenylethyl resorcinol; phenylpropyl resorcinol; p-chlorobenzyl resorcinol; 5-chloro-2,4-dihydroxydiphenyl methane; 4'-chloro-2,4-dihydroxydiphenyl methane; 5-bromo-2,4-dihydroxydiphenyl methane; and 4'-bromo-2,4-dihydroxydiphenyl methane.

Specific bisphenolic antimicrobial agents that can be used in the disclosure include, but are not limited to: 2,2'-methylene bis-(4-chlorophenol); 2,4,4'trichloro-2'-hydroxydiphenyl ether, which is sold by Ciba Geigy, Florham Park, N.J. under the tradename Triclosan®; 2,2'-methylene bis-(3,4,6-trichlorophenol); 2,2'-methylene bis-(4-chloro-6-bromophenol); bis-(2-hydroxy-3,5-dichlorop-henyl) sulphide; and bis-(2-hydroxy-5-chlorobenzyl)sulphide.

Specific benzoic esters (parabens) that can be used in the disclosure include, but are not limited to: methylparaben; propylparaben; butylparaben; ethylparaben; isopropylparaben; isobutylparaben; benzylparaben; sodium methylparaben; and sodium propylparaben.

Specific halogenated carbanilides that can be used in the disclosure include, but are not limited to: 3,4,4'-trichlorocarbanilides, such as 3-(4-chlorophenyl)-1-(3,4-dichlorphenyl)urea sold under the tradename Triclocarban® by Ciba-Geigy, Florham Park, N.J.; 3-trifluoromethyl-4,4'-dichlorocarbanilide; and 3,3',4-trichlorocarbanilide.

Specific polymeric antimicrobial agents that can be used in the disclosure include, but are not limited to: polyhexamethylene biguanide hydrochloride; and poly(iminoimidocarbonyl iminoimidocarbonyl iminohexamethylene hydrochloride), which is sold under the tradename Vantocil® IB.

Specific thazolines that can be used in the disclosure include, but are not limited to that sold under the tradename Micro-Check®; and 2-n-octyl-4-isothiazolin-3-one, which is sold under the tradename Vinyzene® IT-3000 DIDP.

Specific trichloromethylthioimides that can be used in the disclosure include, but are not limited to: N-(trichloromethylthio)phthalimide, which is sold under the tradename Fungitrol®; and N-trichloromethylthio-4-cyclohexene-1,2-dicarboximide, which is sold under the tradename Vancide®.

Specific natural antimicrobial agents that can be used in the disclosure include, but are not limited to, oils of: anise; lemon; orange; rosemary; wintergreen; thyme; lavender; cloves; hops; tea tree; citronella; wheat; barley; lemongrass; cedar leaf; cedarwood; cinnamon; fleagrass; geranium; sandalwood; violet; cranberry; eucalyptus; vervain; peppermint; gum benzoin; basil; fennel; fir; balsam; menthol; ocmea origanuin; hydastis; carradensis; Berberidaceac daceae; Ratanhiae longa; and Curcuma longa. Also included in this class of natural antimicrobial agents are the key chemical components of the plant oils which have been found to provide antimicrobial benefit. These chemicals include, but are not limited to: anethol; catechole; camphene; thymol; eugenol; eucalyptol; ferulic acid; farnesol; hinokitiol; tropolone; limonene; menthol; methyl salicylate; carvacol; terpineol; verbenone; berberine; ratanhiae extract; caryophellene oxide; citronellic acid; curcumin; nerolidol; and geraniol.

Specific metal salts that can be used in the disclosure include, but are not limited to, salts of metals in groups 3a-5a, 3b-7b, and 8 of the periodic table. Specific examples of metal salts include, but are not limited to, salts of: aluminum; zirconium; zinc; silver; gold; copper; lanthanum; tin; mercury; bismuth; selenium; strontium; scandium; yttrium; cerium; praseodymiun; neodymium; promethum; samarium; europium; gadolinium; terbium; dysprosium; holmium; erbium; thalium; ytterbium; lutetium; and mixtures thereof. An example of the metal-ion based antimicrobial agent is sold under the tradename HealthShield®, and is manufactured by HealthShield Technology, Wakefield, Mass. [give other examples here e.g. smith and nephew]

Specific broad-spectrum antimicrobial agents that can be used in the disclosure include, but are not limited to, those that are recited in other categories of antimicrobial agents herein.

Additional antimicrobial agents that can be used in the methods of the disclosure include, but are not limited to: pyrithiones, and in particular pyrithione-including zinc complexes such as that sold under the tradename Octopirox®; dimethyidimethylol hydantoin, which is sold under the tradename Glydant®; methylchloroisothiazolinone/methylisothiazolinone, which is sold under the tradename Kathon CG®; sodium sulfite; sodium bisulfite; imidazolidinyl urea, which is sold under the tradename Germall 115®; diazolidinyl urea, which is sold under the tradename Germall 11®; benzyl alcohol v2-bromo-2-nitropropane-1,3-diol, which is sold under the tradename Bronopol®; formalin or formaldehyde; iodopropenyl butylcarbamate, which is sold under the tradename Polyphase P100®; chloroacetamide; methanamine; methyldibromonitrile glutaronitrile (1,2-dibromo-2,4-dicyanobutane), which is sold under the tradename Tektamer®; glutaraldehyde; 5-bromo-5-nitro-1,3-dioxane, which is sold under the tradename Bronidox®; phenethyl alcohol; o-phenylphenol/sodium o-phenylphenol sodium hydroxymethylglycinate, which is sold under the tradename Suttocide A®; polymethoxy bicyclic oxazolidine; which is sold under the tradename Nuosept C®; dimethoxane; thimersal; dichlorobenzyl alcohol; captan; chlorphenenesin; dichlorophene; chlorbutanol; glyceryl laurate; halogenated diphenyl ethers; 2,4,4'-trichloro-2'-hydroxy-diphenyl ether, which is sold under the tradename Triclosan® and is available from Ciba-Geigy, Florham Park, N.J.; and 2,2'-dihydroxy-5,5'-dibromo-diphenyl ether.

Additional antimicrobial agents that can be used in the methods of the disclosure include those disclosed by U.S. Pat. Nos. 3,141,321; 4,402,959; 4,430,381; 4,533,435; 4,625,026; 4,736,467; 4,855,139; 5,069,907; 5,091,102; 5,639,464; 5,853,883; 5,854,147; 5,894,042; and 5,919,554, and U.S. Pat. Appl. Publ. Nos. 20040009227 and 20110081530.

(g) Collagens and Agents that Promote Collagen Synthesis

The compositions of the present disclosure may include collagens and agents that promote collagen synthesis. Collagen is a fibrous protein produced in dermal fibroblast cells and forming 70% of the dermis. Collagen is responsible for the smoothing and firming of the skin. Therefore, when the synthesis of collagen is reduced, skin aging will occur, and so the firming and smoothing of the skin will be rapidly reduced. As a result, the skin will be flaccid and wrinkled. On the other hand, when metabolism of collagen is activated by the stimulation of collagen synthesis in the skin, the components of dermal matrices will be increased, leading to effects, such as wrinkle improvement, firmness improvement and skin strengthening. Thus, collagens and agents that promote collagen synthesis may also be useful in the present disclosure. Agents that promote collagen synthesis (i.e., pro-collagen synthesis agents) include amino acids, peptides, proteins, lipids, small chemical molecules, natural products and extracts from natural products.

For instance, it was discovered that intake of vitamin C, iron, and collagen can effectively increase the amount of collagen in skin or bone. See, e.g., U.S. Patent Application Publication 20090069217. Examples of the vitamin C include an ascorbic acid derivative such as L-ascorbic acid or sodium L-ascorbate, an ascorbic acid preparation obtained by coating ascorbic acid with an emulsifier or the like, and a mixture containing two or more of those vitamin Cs at an arbitrary rate. In addition, natural products containing vitamin C such as acerola and lemon may also be used. Examples of the iron preparation include: an inorganic iron such as ferrous sulfate, sodium ferrous citrate, or ferric pyrophosphate; an organic iron such as heme iron, ferritin iron, or lactoferrin iron; and a mixture containing two or more of those irons at an arbitrary rate. In addition, natural products containing iron such as spinach or liver may also be used. Moreover, examples of the collagen include: an extract obtained by treating bone, skin, or the like of a mammal such as bovine or swine with an acid or alkaline; a peptide obtained by hydrolyzing the extract with a protease such as pepsine, trypsin, or chymotrypsin; and a mixture containing two or more of those collagens at an arbitrary rate. Collagens extracted from plant sources may also be used.

Additional pro-collagen synthesis agents are described, for example, in U.S. Pat. Nos. 7,598,291, 7,722,904, 6,203, 805, 5,529,769, etc., and U.S. Patent Application Publications 20060247313, 20080108681, 20110130459, 20090325885, 20110086060, etc.

(4) Methods of Use

The biophotonic compositions of the present disclosure have numerous uses. Without being bound by theory, the biophotonic compositions of the present disclosure may promote wound healing or tissue repair. The biophotonic compositions of the present disclosure may also be used to treat a skin disorder. The biophotonic compositions of the present disclosure may also be used to treat acne. The biophotonic compositions of the present disclosure may also be used for skin rejuvenation. The biophotonic compositions of the present disclosure may also be used for treating acute inflammation. Therefore, it is an objective of the present disclosure to provide a method for providing biophotonic therapy to a wound, where the method promotes wound healing. It is also an objective of the present disclosure to provide a method for providing biophotonic therapy to a skin tissue afflicted with acne, wherein the method is used to treat acne. It is also an objective of the present disclosure to provide a method for providing biophotonic therapy to a skin tissue afflicted with a skin disorder, wherein the method is used to treat the skin disorder. It is also an objective of the present disclosure to provide a method for providing biophotonic therapy to skin tissue, wherein the method is used for promoting skin rejuvenation.

In certain embodiments, the present disclosure provides a method for providing a biophotonic therapy to a wound, the method comprising: applying (e.g., by topical application) a biophotonic composition of the present disclosure to a site of a wound, and illuminating the biophotonic composition with light having a wavelength that overlaps with an absorption spectrum of the first xanthene dye (e.g., donor xanthene dye) of the biophotonic composition.

In yet another aspect, the present disclosure provides a method for promoting skin rejuvenation. In certain embodiments, the present disclosure provides a method for providing skin rejuvenation, the method comprising: applying (e.g., by topical application) a biophotonic composition of the present disclosure to the skin, and illuminating the biophotonic composition with light having a wavelength that overlaps with an absorption spectrum of the first xanthene dye (e.g., donor xanthene dye) of the biophotonic composition.

In yet another aspect, the present disclosure provides a method for providing biophotonic therapy to a target skin tissue afflicted with a skin disorder. In certain embodiments, the present disclosure provides a method for providing a biophotonic therapy to a target skin tissue, the method comprising: applying (e.g., by topical application) a biophotonic composition of the present disclosure to a target skin tissue, and illuminating the biophotonic composition with light having a wavelength that overlaps with an absorption spectrum of the first xanthene dye (e.g., donor xanthene dye) of the biophotonic composition.

In yet another aspect, the present disclosure provides a method for providing biophotonic therapy to a target skin tissue afflicted with acne. In certain embodiments, the present disclosure provides a method for providing a biophotonic therapy to a target skin tissue afflicted with acne, the method comprising: applying (e.g., by topical application) a biophotonic composition of the present disclosure to a target skin tissue, and illuminating the biophotonic composition with light having a wavelength that overlaps with an absorption spectrum of the first xanthene dye (e.g., donor xanthene dye) of the biophotonic composition.

In other embodiments, the present disclosure provides a method for treating acute inflammation, the method comprising: topically applying a biophotonic composition of the present disclosure to a target skin tissue with acute inflammation, and illuminating the biophotonic composition with light having a wavelength that overlaps with an absorption spectrum of the first xanthene dye (e.g., donor xanthene dye) of the biophotonic composition.

The biophotonic compositions suitable for use in the methods of the present disclosure may be selected from any of the embodiments of the biophotonic compositions described above. For instance, the biophotonic compositions useful in the method of the present disclosure may comprise a first xanthene dye that undergoes at least partial photobleaching upon application of light. The first xanthene dye may absorb at a wavelength of about 200-800 nm, 200-700 nm, 200-600 nm or 200-500 nm. In one embodiment, the first xanthene dye absorbs at a wavelength of about 200-600 nm. In some embodiments, the first xanthene dye absorbs light at a wavelength of about 200-300 nm, 250-350 nm, 300-400 nm, 350-450 nm, 400-500 nm, 450-650 nm, 600-700 nm, 650-750 nm or 700-800 nm. The absorption spectrum of the second xanthene dye should overlap at least about 80%, 50%, 40%, 30%, or 20% with the emission spectrum of the first xanthene dye. In some embodiments, the first xanthene dye has an emission spectrum that overlaps at least 1-10%, 5-15%, 10-20%, 15-25%, 20-30%, 25-35%, 30-40%, 35-45%, 50-60%, 55-65% or 60-70% with an absorption spectrum of the second xanthene dye.

Illumination of the biophotonic composition with light may cause a transfer of energy from the first xanthene dye to the second xanthene dye. Subsequently, the second xanthene dye may emit energy as fluorescence and/or generate reactive oxygen species. In certain embodiments of the methods the present disclosure, energy transfer caused by the application of light is not accompanied by concomitant generation of heat, or does not result in tissue damage.

The biophotonic compositions useful for the present methods can be formulated with any carrier. In certain embodiments, the carrier is a gelling agent. The gelling agent may include, but is not limited to, lipids such as glycerin, glycols such as propylene glycol, hyaluronic acid, glucosamine sulfate, cellulose derivatives (hydroxypropyl methylcellulose, hydroxyethyl cellulose, hydroxypropyl cellulose, methylcellulose and the like), noncellulose polysaccharides (galactomannans, guar gum, carob gum, gum arabic, sterculia gum, agar, alginates and the like) and acrylic acid polymers.

In the methods of the present disclosure, any source of actinic light can be used. Any type of halogen, LED or plasma arc lamp or laser may be suitable. The primary characteristic of suitable sources of actinic light will be that they emit light in a wavelength (or wavelengths) appropriate for activating the one or more chromophores present in the composition. In one embodiment, an argon laser is used. In another embodiment, a potassium-titanyl phosphate (KTP) laser (e.g. a GreenLight™ laser) is used. In another embodiment, sunlight may be used. In yet another embodiment, a LED photocuring device is the source of the actinic light. In yet another embodiment, the source of the actinic light is a source of light having a wavelength between about 200 to 800 nm. In another embodiment, the source of the actinic light is a source of visible light having a wavelength between about 400 and 600 nm. Furthermore, the source of actinic light should have a suitable power density. Suitable power density for non-collimated light sources (LED, halogen or plasma lamps) are in the range from about 1 mW/cm$^2$ to about 200 mW/cm$^2$. Suitable power density for laser light sources are in the range from about 0.5 mW/cm$^2$ to about 0.8 mW/cm$^2$.

In some embodiments of the methods of the present disclosure, the light has an energy at the subject's skin, wound or mucosa surface of between about 1 mW/cm$^2$ and about 500 mW/cm$^2$, 1-300 mW/cm$^2$, or 1-200 mW/cm$^2$, wherein the energy applied depends at least on the condition being treated, the wavelength of the light, the distance of the subject's skin from the light source, and the thickness of the biophotonic composition. In certain embodiments, the light at the subject's skin is between about 1-40 mW/cm$^2$, or 20-60 mW/cm$^2$, or 40-80 mW/cm$^2$, or 60-100 mW/cm$^2$, or 80-120 mW/cm$^2$, or 100-140 mW/cm$^2$, or 120-160 mW/cm$^2$, or 140-180 mW/cm$^2$, or 160-200 mW/cm$^2$, or 110-240 mW/cm$^2$, or 110-150 mW/cm$^2$, or 190-240 mW/cm$^2$.

In some embodiments, a mobile device can be used to activate embodiments of the biophotonic composition of the present disclosure, wherein the mobile device can emit light having an emission spectra which overlaps an absorption spectra of the donor xanthene dye in the biophotonic composition. The mobile device can have a display screen through which the light is emitted and/or the mobile device can emit light from a flashlight which can photoactivate the biophotonic composition.

In some embodiments, a display screen on a television or a computer monitor can be used to activate the biophotonic composition, wherein the display screen can emit light having an emission spectra which overlaps an absorption spectra of the donor xanthene dye in the biophotonic composition.

In certain embodiments, the first and/or the second xanthene dye can be photoactivated by ambient light which may originate from the sun or other light sources. Ambient light can be considered to be a general illumination that comes from all directions in a room that has no visible source. In certain embodiments, the first and/or the second xanthene dye can be photoactivated by light in the visible range of the electromagnetic spectrum. Exposure times to ambient light may be longer than that to direct light.

In certain embodiments, different sources of light can be used to activate the biophotonic compositions, such as a combination of ambient light and direct LED light.

The duration of the exposure to actinic light required will be dependent on the surface of the treated area, the type of lesion, trauma or injury that is being treated, the power density, wavelength and bandwidth of the light source, the thickness of the biophotonic composition, and the treatment distance from the light source. The illumination of the treated area by fluorescence may take place within seconds or even fragment of seconds, but a prolonged exposure period is beneficial to exploit the synergistic effects of the absorbed, reflected and reemitted light on the composition of the present disclosure and its interaction with the tissue being treated. In one embodiment, the time of exposure to actinic light of the tissue, skin or wound on which the biophotonic composition has been applied is a period between 1 minute and 5 minutes. In another embodiment, the time of exposure to actinic light of the tissue, skin or wound on which the biophotonic composition has been applied is a period between 1 minute and 5 minutes. In some other embodiments, the biophotonic composition is illuminated for a period between 1 minute and 3 minutes. In certain embodiments, light is applied for a period of 1-30 seconds, 15-45 seconds, 30-60 seconds, 0.75-1.5 minutes, 1-2 minutes, 1.5-2.5 minutes, 2-3 minutes, 2.5-3.5 minutes, 3-4 minutes, 3.5-4.5 minutes, 4-5 minutes, 5-10 minutes, 10-15 minutes, 15-20 minutes, 20-25 minutes, or 20-30 minutes. In yet another embodiment, the source of actinic light is in continuous motion over the treated area for the appropriate time of exposure. In yet another embodiment, multiple applications of the biophotonic composition and actinic light are performed. In some embodiments, the tissue, skin or wound is exposed to actinic light at least two, three, four, five or six times. In some embodiments, a fresh application of the biophotonic composition is applied before exposure to actinic light.

In the methods of the present disclosure, the biophotonic composition may be optionally removed from the site of treatment following application of light. In certain embodiments, the biophotonic composition is left on the treatment site for more than 30 minutes, more than one hour, more than 2 hours, more than 3 hours. It can be illuminated with ambient light. To prevent drying, the composition can be covered with a transparent or translucent cover such as a polymer film, or an opaque cover which can be removed before illumination.

(5) Wounds and Wound Healing

The biophotonic compositions and methods of the present disclosure may be used to treat wounds and promote wound healing. Wounds that may be treated by the biophotonic compositions and methods of the present disclosure include, for example, injuries to the skin and subcutaneous tissue initiated in different ways (e.g., pressure ulcers from extended bed rest, wounds induced by trauma, wounds induced by conditions such as periodontitis) and with varying characteristics. In certain embodiments, the present disclosure provides biophotonic compositions and methods for treating and/or promoting the healing of, for example, burns, incisions, excisions, lacerations, abrasions, puncture or penetrating wounds, surgical wounds, contusions, hematomas, crushing injuries, gun shots, sores and ulcers.

Biophotonic compositions and methods of the present disclosure may be used to treat and/or promote the healing of chronic cutaneous ulcers or wounds, which are wounds that have failed to proceed through an orderly and timely series of events to produce a durable structural, functional, and cosmetic closure. The vast majority of chronic wounds can be classified into three categories based on their etiology: pressure ulcers, neuropathic (diabetic foot) ulcers and vascular (venous or arterial) ulcers.

In certain other embodiments, the present disclosure provides biophotonic compositions and methods for treating and/or promoting healing, Grade I-IV ulcers. In certain embodiments, the application provides compositions suitable for use with Grade II ulcers in particular. Ulcers may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum).

For example, the present disclosure provides biophotonic compositions and methods for treating and/or promoting healing of a diabetic ulcer. Diabetic patients are prone to foot and other ulcerations due to both neurologic and vascular complications. Peripheral neuropathy can cause altered or complete loss of sensation in the foot and/or leg. Diabetic patients with advanced neuropathy lose all ability for sharp-dull discrimination. Any cuts or trauma to the foot may go completely unnoticed for days or weeks in a patient with neuropathy. A patient with advanced neuropathy loses the ability to sense a sustained pressure insult, as a result, tissue ischemia and necrosis may occur leading to for example, plantar ulcerations. Microvascular disease is one of the significant complications for diabetics which may also lead to ulcerations. In certain embodiments, compositions and methods of treating a chronic wound are provided here in, where the chronic wound is characterized by diabetic foot ulcers and/or ulcerations due to neurologic and/or vascular complications of diabetes.

In other examples, the present disclosure provides biophotonic compositions and methods for treating and/or promoting healing of a pressure ulcer. Pressure ulcer includes bed sores, decubitus ulcers and ischial tuberosity ulcers and can cause considerable pain and discomfort to a patient. A pressure ulcer can occur as a result of a prolonged pressure applied to the skin. Thus, pressure can be exerted on the skin of a patient due to the weight or mass of an individual. A pressure ulcer can develop when blood supply to an area of the skin is obstructed or cut off for more than two or three hours. The affected skin area can turns red, becomes painful and can become necrotic. If untreated, the skin breaks open and can become infected. An ulcer sore is therefore a skin ulcer that occurs in an area of the skin that is under pressure from e.g. lying in bed, sitting in a wheelchair, and/or wearing a cast for a prolonged period of time. Pressure ulcer can occur when a person is bedridden, unconscious, unable to sense pain, or immobile. Pressure ulcer often occur in boney prominences of the body such as the buttocks area (on the sacrum or iliac crest), or on the heels of a foot.

In other examples, the present disclosure provides biophotonic compositions and methods for treating and/or promoting healing of acute wounds.

Additional types of wound that can be treated by the biophotonic compositions and methods of the present disclosure include those disclosed by U.S. Pat. Appl. Publ. No. 20090220450, which is incorporated herein by reference.

Wound healing in adult tissues is a complicated reparative process. For example, the healing process for skin involves the recruitment of a variety of specialized cells to the site of the wound, extracellular matrix and basement membrane deposition, angiogenesis, selective protease activity and re-epithelialization.

There are three distinct phases in the wound healing process. First, in the inflammatory phase, which typically occurs from the moment a wound occurs until the first two to five days, platelets aggregate to deposit granules, promoting the deposit of fibrin and stimulating the release of growth factors. Leukocytes migrate to the wound site and begin to digest and transport debris away from the wound. During this inflammatory phase, monocytes are also converted to macrophages, which release growth factors for stimulating angiogenesis and the production of fibroblasts.

Second, in the proliferative phase, which typically occurs from two days to three weeks, granulation tissue forms, and epithelialization and contraction begin. Fibroblasts, which are key cell types in this phase, proliferate and synthesize collagen to fill the wound and provide a strong matrix on which epithelial cells grow. As fibroblasts produce collagen, vascularization extends from nearby vessels, resulting in granulation tissue. Granulation tissue typically grows from the base of the wound. Epithelialization involves the migration of epithelial cells from the wound surfaces to seal the wound. Epithelial cells are driven by the need to contact cells of like type and are guided by a network of fibrin strands that function as a grid over which these cells migrate. Contractile cells called myofibroblasts appear in wounds, and aid in wound closure. These cells exhibit collagen synthesis and contractility, and are common in granulating wounds.

Third, in the remodeling phase, the final phase of wound healing which can take place from three weeks up to several years, collagen in the scar undergoes repeated degradation and re-synthesis. During this phase, the tensile strength of the newly formed skin increases.

However, as the rate of wound healing increases, there is often an associated increase in scar formation. Scarring is a consequence of the healing process in most adult animal and human tissues. Scar tissue is not identical to the tissue which it replaces, as it is usually of inferior functional quality. The types of scars include, but are not limited to, atrophic, hypertrophic and keloidal scars, as well as scar contractures. Atrophic scars are flat and depressed below the surrounding skin as a valley or hole. Hypertrophic scars are elevated scars that remain within the boundaries of the original lesion, and often contain excessive collagen arranged in an abnormal pattern. Keloidal scars are elevated scars that spread beyond the margins of the original wound and invade the surrounding normal skin in a way that is site specific, and often contain whorls of collagen arranged in an abnormal fashion.

In contrast, normal skin consists of collagen fibers arranged in a basket-weave pattern, which contributes to both the strength and elasticity of the dermis. Thus, to achieve a smoother wound healing process, an approach is needed that not only stimulates collagen production, but also does so in a way that reduces scar formation.

The biophotonic compositions and methods of the present disclosure promote the wound healing by promoting the formation of substantially uniform epithelialization; promoting collagen synthesis; promoting controlled contraction; and/or by reducing the formation of scar tissue. In certain embodiments, the biophotonic compositions and methods of the present disclosure may promote wound healing by promoting the formation of substantially uniform epithelialization. In some embodiments, the biophotonic compositions and methods of the present disclosure promote collagen synthesis. In some other embodiments, the biophotonic compositions and methods of the present disclosure promote controlled contraction. In certain embodiments, the biophotonic compositions and methods of the present disclosure promote wound healing, for example, by reducing the formation of scar tissue or by speeding up the wound closure process. In certain embodiments, the biophotonic compositions and methods of the present disclosure promote wound healing, for example, by reducing inflammation. In certain embodiments, the biophotonic composition can be used following wound closure to optimize scar revision. In this case, the biophotonic composition may be applied at regular intervals such as once a week, or at an interval deemed appropriate by the physician.

The biophotonic composition may be soaked into a woven or non-woven material or a sponge and applied as a wound dressing. A light source, such as LEDs or waveguides, may be provided within or adjacent the wound dressing or the composition to illuminate the composition. The waveguides can be optical fibres which can transmit light, not only from their ends, but also from their body. For example, made of polycarbonate or polymethylmethacrylate.

Adjunct therapies which may be topical or systemic such as antibiotic treatment may also be used. Negative pressure assisted wound closure can also be used to assist wound closure and/or to remove the composition.

(6) Acne and Acne Scars

The biophotonic compositions and methods of the present disclosure may be used to treat acne. As used herein, "acne" means a disorder of the skin caused by inflammation of skin glands or hair follicles. The biophotonic compositions and methods of the disclosure can be used to treat acne at early pre-emergent stages or later stages where lesions from acne are visible. Mild, moderate and severe acne can be treated with embodiments of the biophotonic compositions and methods. Early pre-emergent stages of acne usually begin with an excessive secretion of sebum or dermal oil from the sebaceous glands located in the pilosebaceous apparatus. Sebum reaches the skin surface through the duct of the hair follicle. The presence of excessive amounts of sebum in the duct and on the skin tends to obstruct or stagnate the normal flow of sebum from the follicular duct, thus producing a thickening and solidification of the sebum to create a solid plug known as a comedone. In the normal sequence of developing acne, hyperkeratinazation of the follicular opening is stimulated, thus completing blocking of the duct. The usual results are papules, pustules, or cysts, often contaminated with bacteria, which cause secondary infections. Acne is characterized particularly by the presence of comedones, inflammatory papules, or cysts. The appearance of acne may range from slight skin irritation to pitting and even the development of disfiguring scars. Accordingly, the biophotonic compositions and methods of the present disclosure can be used to treat one or more of skin irritation, pitting, development of scars, comedones, inflammatory papules, cysts, hyperkeratinazation, and thickening and hardening of sebum associated with acne.

The composition may be soaked into or applied to a woven or non-woven material or a sponge and applied as a mask to body parts such as the face, body, arms, legs etc. A light source, such as LEDs or waveguides, may be provided within or adjacent the mask or the composition to illuminate the composition. The waveguides can be optical fibres which can transmit light, not only from their ends, but also from their body. For example, made of polycarbonate or polymethylmethacrylate.

The biophotonic compositions and methods of the present disclosure may be used to treat various types of acne. Some types of acne include, for example, acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, and nodulocystic acne.

(7) Skin Aging and Rejuvenation

The dermis is the second layer of skin, containing the structural elements of the skin, the connective tissue. There are various types of connective tissue with different functions. Elastin fibers give the skin its elasticity, and collagen gives the skin its strength.

The junction between the dermis and the epidermis is an important structure. The dermal-epidermal junction interlocks forming finger-like epidermal ridges. The cells of the epidermis receive their nutrients from the blood vessels in the dermis. The epidermal ridges increase the surface area of the epidermis that is exposed to these blood vessels and the needed nutrients.

The aging of skin comes with significant physiological changes to the skin. The generation of new skin cells slows down, and the epidermal ridges of the dermal-epidermal junction flatten out. While the number of elastin fibers increases, their structure and coherence decrease. Also the amount of collagen and the thickness of the dermis decrease with the ageing of the skin.

Collagen is a major component of the skin's extracellular matrix, providing a structural framework. During the aging process, the decrease of collagen synthesis and insolubilization of collagen fibers contribute to a thinning of the dermis and loss of the skin's biomechanical properties.

The physiological changes to the skin result in noticeable aging symptoms often referred to as chronological-, intrinsic- and photo-ageing. The skin becomes drier, roughness and scaling increase, the appearance becomes duller, and most obviously fine lines and wrinkles appear. Other symptoms or signs of skin aging include, but are not limited to, thinning and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, a blotchy complexion.

The dermal-epidermal junction is a basement membrane that separates the keratinocytes in the epidermis from the extracellular matrix, which lies below in the dermis. This membrane consists of two layers: the basal lamina in contact with the keratinocytes, and the underlying reticular lamina in contact with the extracellular matrix. The basal lamina is rich in collagen type IV and laminin, molecules that play a role in providing a structural network and bioadhesive properties for cell attachment.

Laminin is a glycoprotein that only exists in basement membranes. It is composed of three polypeptide chains (alpha, beta and gamma) arranged in the shape of an asymmetric cross and held together by disulfide bonds. The three chains exist as different subtypes which result in twelve different isoforms for laminin, including Laminin-1 and Laminin-5.

The dermis is anchored to hemidesmosomes, specific junction points located on the keratinocytes, which consist of α-integrins and other proteins, at the basal membrane keratinocytes by type VII collagen fibrils. Laminins, and particularly Laminin-5, constitute the real anchor point between hemidesmosomal transmembrane proteins in basal keratinocytes and type VII collagen.

Laminin-5 synthesis and type VII collagen expression have been proven to decrease in aged skin. This causes a loss of contact between dermis and epidermis, and results in the skin losing elasticity and becoming saggy.

Recently another type of wrinkles generally referred to as expression wrinkles, got general recognition. These wrinkles require loss of resilience, particularly in the dermis, because of which the skin is no longer able to resume its original state when facial muscles which produce facial expressions exert stress on the skin, resulting in expression wrinkles.

The compositions and methods of the present disclosure promote skin rejuvenation. In certain embodiments, the compositions and methods of the present disclosure promote collagen synthesis. In certain other embodiments, the compositions and methods of the present disclosure may reduce, diminish, retard or even reverse one or more signs of skin aging including, but not limited to, appearance of fine lines or wrinkles, thin and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, or a blotchy complexion. In certain embodiments, the compositions and methods of the present disclosure may induce a reduction in pore size, enhance sculpturing of skin subsections, and/or enhance skin translucence.

(8) Skin Disorders

The biophotonic compositions and methods of the present disclosure may be used to treat skin disorders that include, but are not limited to, erythema, telangiectasia, actinic telangiectasia, psoriasis, skin cancer, pemphigus, sunburn, dermatitis, eczema, rashes, impetigo, lichen simplex chronicus, rhinophyma, perioral dermatitis, pseudofolliculitis barbae, drug eruptions, erythema multiforme, erythema nodosum, granuloma annulare, actinic keratosis, purpura, alopecia areata, aphthous stomatitis, drug eruptions, dry skin, chapping, xerosis, ichthyosis vulgaris, fungal infections, parasitic infection, viral infections, herpes simplex, intertrigo, keloids, keratoses, milia, moluscum contagiosum, pityriasis rosea, pruritus, urticaria, and vascular tumors and malformations. Dermatitis includes contact dermatitis, atopic dermatitis, seborrheic dermatitis, nummular dermatitis, generalized exfoliative dermatitis, and statis dermatitis. Skin cancers include melanoma, basal cell carcinoma, and squamous cell carcinoma.

Some skin disorders present various symptoms including redness, flushing, burning, scaling, pimples, papules, pustules, comedones, macules, nodules, vesicles, blisters, telangiectasia, spider veins, sores, surface irritations or pain, itching, inflammation, red, purple, or blue patches or discolorations, moles, and/or tumors. Accordingly, the biophotonic compositions and methods of the present disclosure can be used to treat redness, flushing, burning, scaling, pimples, papules, pustules, comedones, macules, nodules, vesicles, blisters, telangiectasia, spider veins, sores, surface irritations or pain, itching, acute inflammation, red, purple, or blue patches or discolorations, moles, and/or tumors. Acute inflammation can present itself as pain, heat, redness, swelling and loss of function. It includes those seen in allergic reactions such as insect bites e.g.; mosquito, bees, wasps, poison ivy, post-ablative treatment.

The composition may be soaked into or applied to a woven or non-woven material or a sponge and applied as a mask to body parts to treat skin disorders. A light source, such as LEDs or waveguides, may be provided within or adjacent the mask or the composition to illuminate the composition. The waveguides can be optical fibres which can transmit light, not only from their ends, but also from their body. For example, made of polycarbonate or polymethylmethacrylate.

(9) Kits

The present disclosure also provides kits for preparing and/or applying any of the compositions of the present disclosure. The kit may include a biophotonic topical composition of the present disclosure. The composition may include an oxygen-releasing agent present in amount about 0.01%-40%, 0.01%-1.0%, 0.5%-10.0%, 5%-15%, 10%-20%, 15%-25%, 20%-30%, 15.0%-25%, 20%-30%, 25%-35%, or 30%-40% by weight to weight of the composition. The first xanthene dye may be present in an amount of about 0.01-40% per weight of the composition, and a second xanthene dye may be present in an amount of about 0.01-40% per weight of the composition. In certain embodiments, the first xanthene dye is present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the second xanthene dye is present in an amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40% per weight of the composition. In certain embodiments, the amount of xanthene dyes may be in the amount of about 0.05-40.05% per weight of the composition. In certain embodiments, the amount of xanthene dyes may be in the amount of about 0.001-0.1%, 0.05-1%, 0.5-2%, 1-5%, 2.5-7.5%, 5-10%, 7.5-12.5%, 10-15%, 12.5-17.5%, 15-20%, 17.5-22.5%, 20-25%, 22.5-27.5%, 25-30%, 27.5-32.5%, 30-35%, 32.5-37.5%, or 35-40.05% per weight of the composition.

In some embodiments, the kit includes more than one composition, for example, a first and a second composition. The first composition may include the oxygen-releasing agent and the second composition may include the xanthene dyes in a liquid or as a powder. In some embodiments, the kit includes containers comprising the compositions of the present disclosure.

The composition (s) may be contained in containers. The containers may be light impermeable, air-tight and/or leak resistant. Exemplary containers include, but are not limited to, syringes, vials, or pouches. For example, the container may be a dual-chamber syringe where the contents of the chambers mix on expulsion of the compositions from the chambers. In another example, the pouch may include two chambers separated by a frangible membrane. In another example, one component may be contained in a syringe and injectable into a container comprising the second component. The container may be a spray can which may or may not be pressurized. The composition may be in liquid and/or gaseous form.

The biophotonic composition may also be provided in a container comprising one or more chambers for holding one or more components of the biophotonic composition, and an outlet in communication with the one or more chambers for discharging the biophotonic composition from the container.

In other embodiments, the kit comprises a systemic or topical drug for augmenting the treatment of the composition. For example, the kit may include a systemic or topical antibiotic or hormone treatment for acne treatment or wound healing.

Written instructions on how to use the biophotonic composition in accordance with the present disclosure may be included in the kit, or may be included on or associated with the containers comprising the compositions of the present disclosure.

In certain embodiments, the kit may comprise a further component which is a dressing. The dressing may be a porous or semi-porous structure for receiving the biophotonic composition. The dressing may comprise woven or non-woven fibrous materials.

In certain embodiments of the kit, the kit may further comprise a light source such as a portable light with a wavelength appropriate to activate the chromophore in the biophotonic composition. The portable light may be battery operated or re-chargeable.

In certain embodiments, the kit may further comprise one or more waveguides.

Identification of equivalent compositions, methods and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLES

The examples below are given so as to illustrate the practice of various embodiments of the present disclosure. They are not intended to limit or define the entire scope of this disclosure.

Example 1

Absorption/Emission Spectra of Fluorescein and Eosin Y in a Gel

The photodynamic properties of (i) Fluorescein sodium salt at about 0.09 mg/mL, (ii) Eosin Y at about 0.305 mg/mL, and (iii) a mixture of Fluorescein sodium salt at about 0.09 mg/mL and Eosin Y at about 0.305 mg/mL, all in a gel (comprising about 12% carbamide peroxide), were evaluated. A flexstation 384 II spectrophotometer was used to measure emitted fluorescence with the following parameters: mode fluorescence, excitation 460 nm, emission spectra 465-750 nm. The absorbance was read using a synergy HT microplate reader: mode absorbance; spectra between 300-650 nm.

Figure 5A:
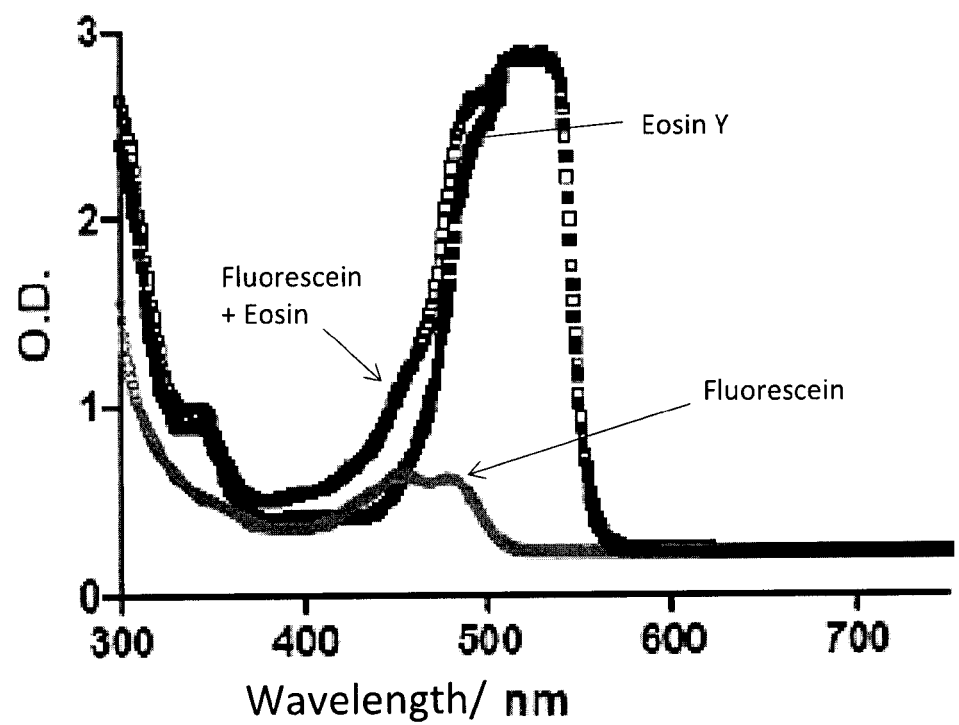
FIGS. 5A and 5B are absorbance and emission spectra, respectively, of (i) Fluorescein sodium salt at about 0.09 mg/mL, (ii) Eosin Y at about 0.305 mg/mL, and (iii) a mixture of Fluorescein sodium salt at about 0.09 mg/mL and Eosin Y at about 0.305 mg/mL, all in a carbamide gel (Example 1).
Figure 5B:
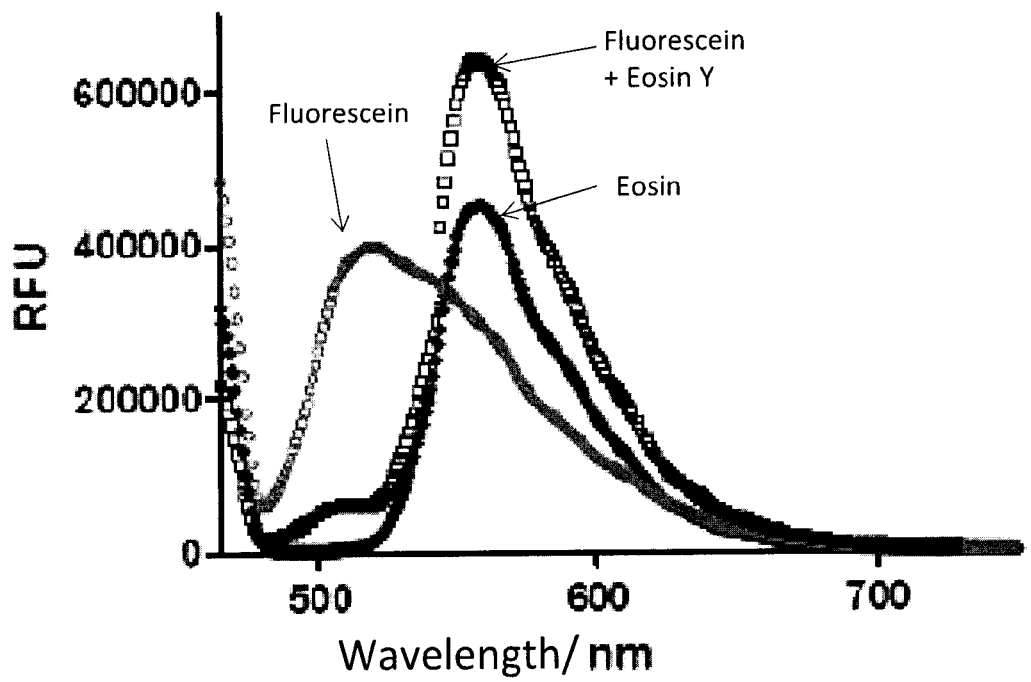

The absorption and emission spectra are shown in FIGS. 5A and 5B which indicate an energy transfer between the chromophores in the combination. In particular a broader absorption and emission spectra was achieved with the Eosin Y and chromophore combination, compared with the individual chromophores. This means that the multiple chromophore composition can be activated with a broader bandwidth of light, and that the multiple chromophore light can emit a broader bandwidth of light after illumination. In other words, emission from the multi-chromophore composition occurred in a broader range of wavelengths compared to the individual chromophores. In this example, the composition emitted light in the green, yellow and orange wavelengths of the visible spectra. Photobleaching of Eosin Y was observed during illumination. Furthermore, results (not shown) indicate that the presence of peroxide in the gel does not affect the absorbance and emission spectra. Peroxide is optional in compositions and methods of the present disclosure.

Example 2

Absorption/Emission Spectra of a Fluorescein and Eosin Y Aqueous Solution

The photodynamic properties of (i) Fluorescein sodium salt at 0.18 mg/mL final concentration, (ii) Eosin Y at about 0.305 mg/mL, and (iii) a mixture of Fluorescein sodium salt at about 0.18 mg/mL and Eosin Y at about 0.305 mg/mL, all in an aqueous solution were evaluated. A flexstation 384 II spectrophotometer was used to measure emitted fluorescence with the following parameters: mode fluorescence, excitation 460 nm, emission spectra 465-750 nm. The absorbance was read using a synergy HT microplate reader: mode absorbance; spectra between 300-650 nm.

Figure 6A:
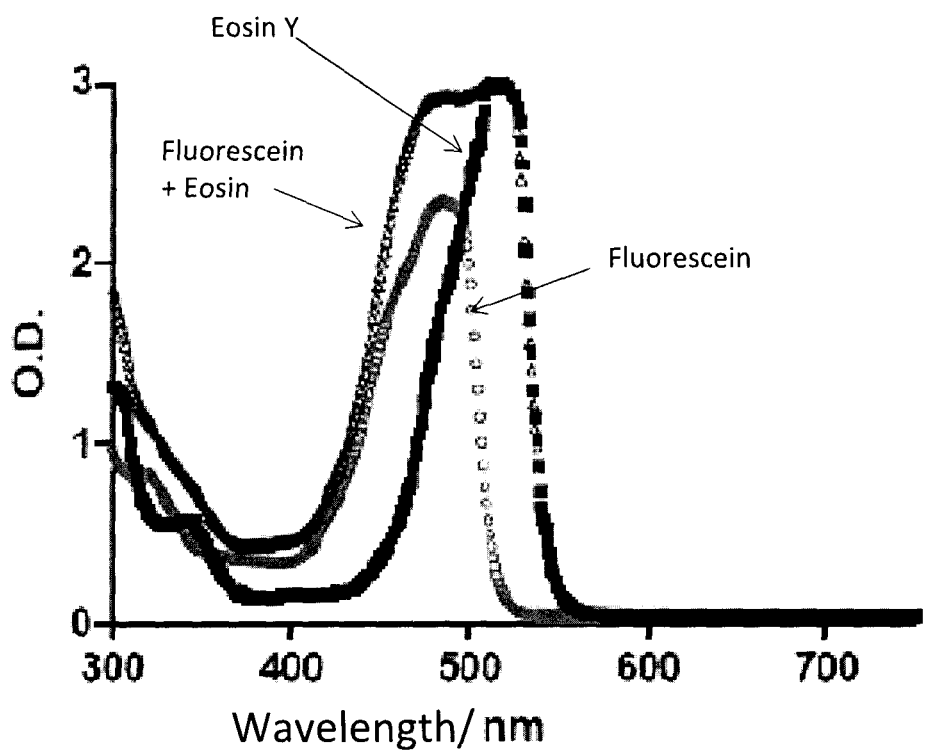
FIGS. 6A and 6B are absorbance and emission spectra, respectively, (i) Fluorescein sodium salt at 0.18 mg/mL final concentration, (ii) Eosin Y at about 0.305 mg/mL, and (iii) a mixture of Fluorescein sodium salt at about 0.18 mg/mL and Eosin Y at about 0.305 mg/mL, all in an aqueous solution (Example 2).
Figure 6B:
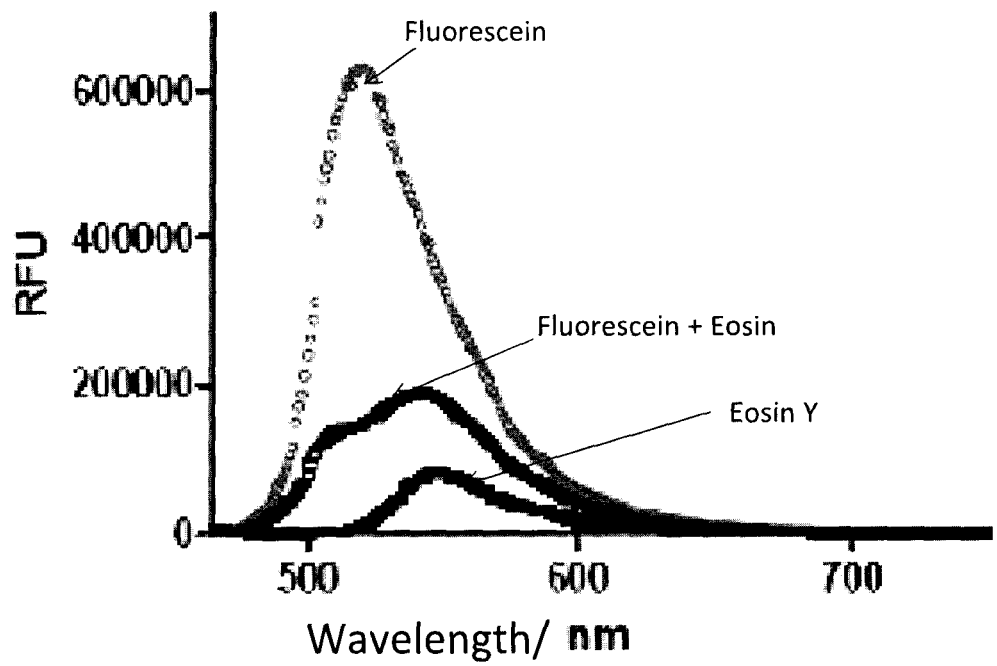

The absorption and emission spectra are shown in FIGS. 6A and 6B which indicate an energy transfer between the chromophores in the combination. Also, as with FIGS. 5A and 5B, a broader emission spectra was achieved with the Eosin Y and chromophore combination, compared with the individual chromophores. The composition emitted light in the green, yellow and orange wavelengths of the visible spectra. The difference in the absorption and emission spectra between Examples 1 and 2 may be explained by the optical difference in the media (gel in Example 1 and aqueous solution in this example) as well as possibly the effect of doubling the fluorescein concentration. It can be seen that adding Fluorescein to Eosin Y, broadens the bandwidth of the absorption and emission peaks of Eosin Y. This confers on the multiple chromophore combination, the ability to absorb a broader range of wavelengths for photoactivation and to emit a wider range of wavelengths which may confer different therapeutic effects at the same time. Photobleaching of Eosin Y was observed during illumination.

Example 3

Absorption/Emission Spectra of Phloxine B and Eosin Y in a Gel

The photodynamic properties of (i) Phloxine B at 0.25 mg/mL final concentration, (ii) Eosin Y at about 0.05 mg/mL, and (iii) a mixture of Phloxine B (0.25 mg/mL) and Eosin Y (0.05 mg/mL), all in a 12% carbamide gel were evaluated. A flexstation 384 II spectrophotometer was used to measure emitted fluorescence with the following parameters: mode fluorescence, excitation 460 nm, emission spectra 465-750 nm. The absorbance was read using a synergy HT microplate reader: mode absorbance; spectra between 300-650 nm.

Figure 7A:
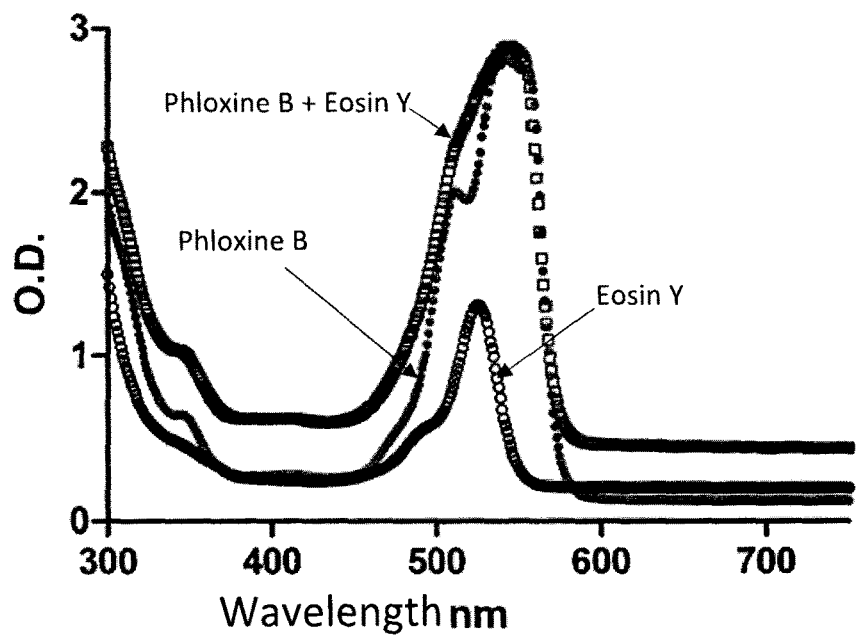
FIGS. 7A and 7B are absorbance and emission spectra, respectively, of (i) Phloxine B at 0.25 mg/mL final concentration, (ii) Eosin Y at about 0.05 mg/mL, and (iii) a mixture of Phloxine B (0.25 mg/mL) and Eosin Y (0.05 mg/mL), all in a 12% carbamide gel (Example 3).
Figure 7B:
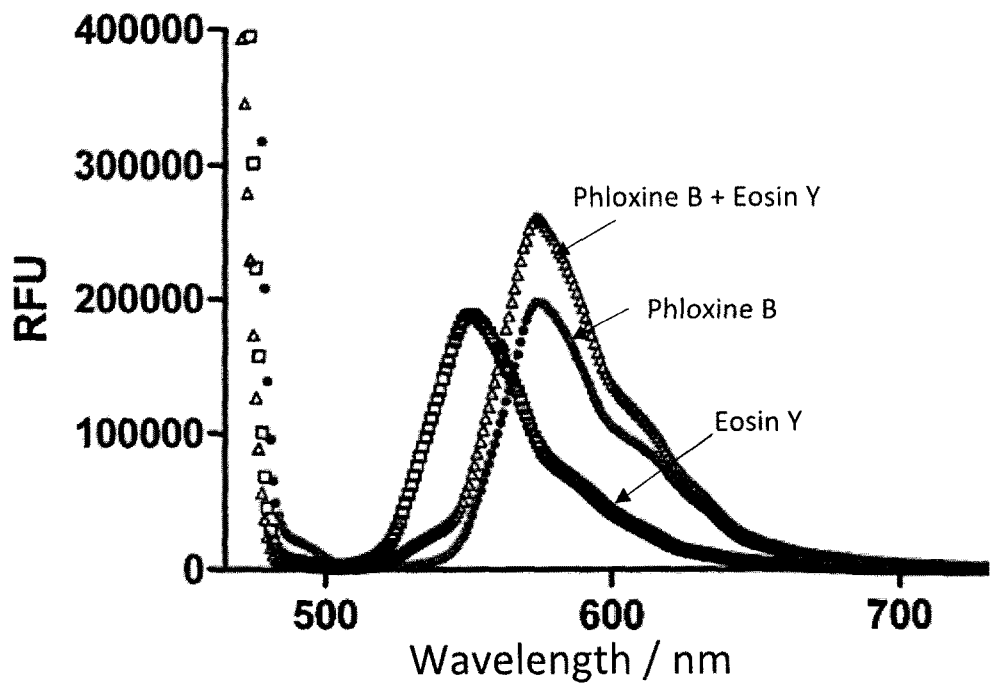

The absorption and emission spectra are shown in FIGS. 7A and 7B which indicate an energy transfer between the chromophores in the combination. As before, broader absorption and emission spectra were achieved with the Phloxine B and Eosin Y chromophore combination, compared with the individual chromophores. The composition emitted light in the green, yellow, orange and red wavelengths of the visible spectra.

Example 4

Absorption/Emission Spectra of an Aqueous Solution of Phloxine B and Eosin Y

The photodynamic properties of (i) Phloxine B at 0.25 mg/mL final concentration, (ii) Eosin Y at about 0.08 mg/mL, and (iii) a mixture of Phloxine B (0.25 mg/mL) and Eosin Y (0.08 mg/mL), all in an aqueous solution were evaluated. A flexstation 384 II spectrophotometer was used to measure emitted fluorescence with the following parameters: mode fluorescence, excitation 460 nm, emission spectra 465-750 nm. The absorbance was read using a synergy HT microplate reader: mode absorbance; spectra between 300-650 nm.

Figure 8A:
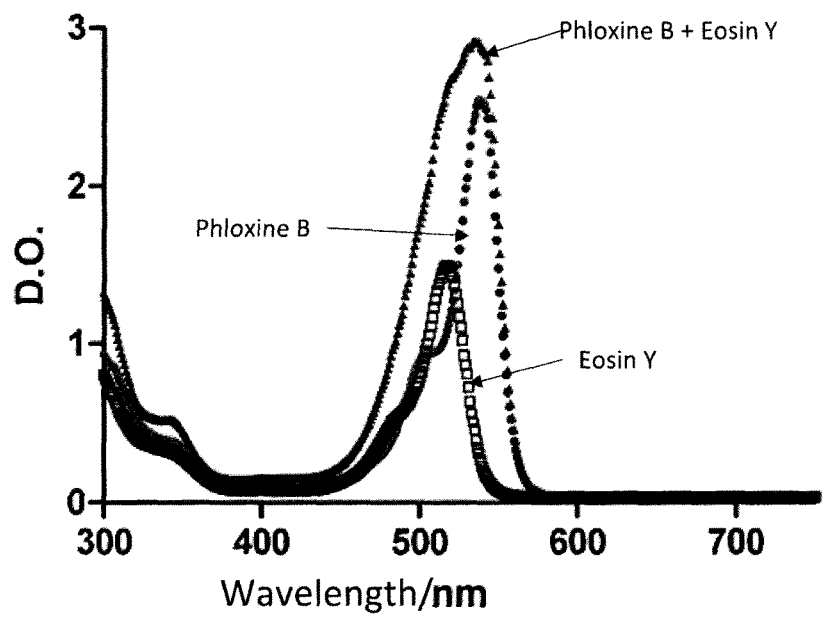
FIGS. 8A and 8B are absorbance and emission spectra, respectively, of (i) Phloxine B at 0.25 mg/mL final concentration, (ii) Eosin Y at about 0.08 mg/mL, and (iii) a mixture of Phloxine B (0.25 mg/mL) and Eosin Y (0.08 mg/mL), all in an aqueous solution (Example 4).
Figure 8B:
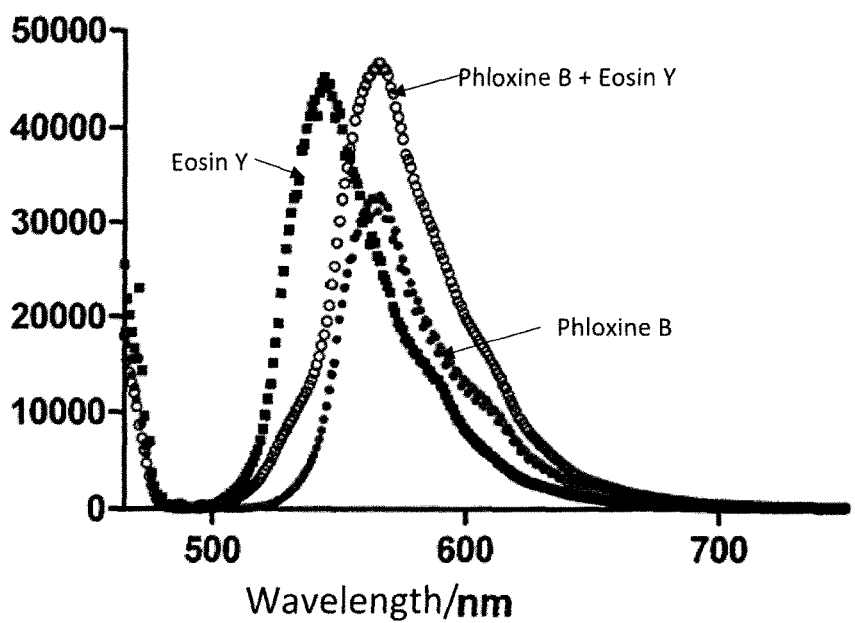

The absorption and emission spectra are shown in FIGS. 8A and 8B which indicate an energy transfer between the chromophores in the combination. Broader absorption and emission spectra were achieved with the Phloxine B and Eosin Y chromophore combination, compared with the individual chromophores. The composition emitted light in the green, yellow, orange and red wavelengths of the visible spectra.

Example 5

Absorption/Emission Spectra of Phloxine B and Fluorescein in a Gel

The photodynamic properties of (i) Fluorescein at about 100 µg/g final concentration, (ii) Phloxine B at about 100 µg/g, and (iii) a mixture of Fluorescein (100 µg/g) and Phloxine B (100 µg/g), all in a 12% carbamide gel were evaluated. A flexstation 384 II spectrophotometer was used to measure emitted fluorescence with the following parameters: mode fluorescence, excitation 460 nm, emission spectra 465-750 nm. The absorbance was read using a synergy HT microplate reader: mode absorbance; spectra between 300-650 nm.

Figure 9A:
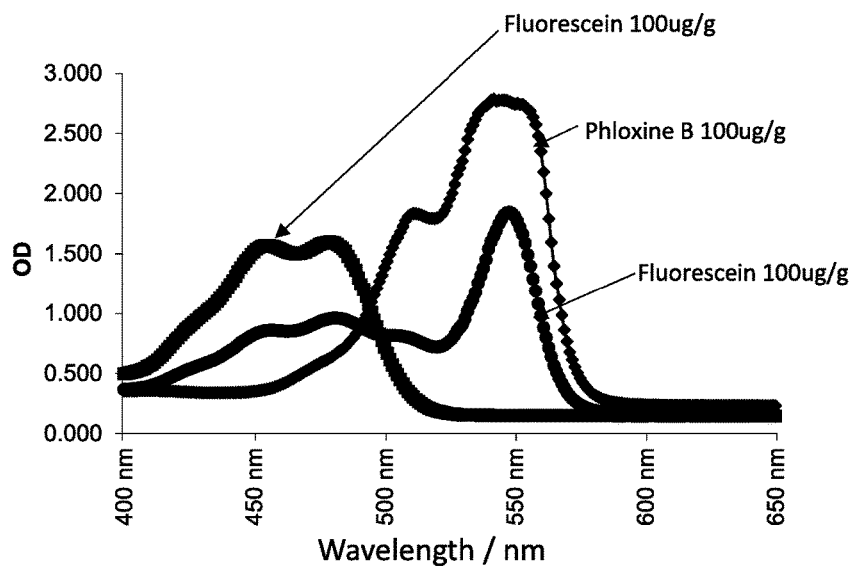
FIGS. 9A and 9B are absorbance and emission spectra, respectively, of (i) Phloxine B at 100 µg/g, (ii) Fluorescein at about 100 µg/g, and (iii) a mixture of Phloxine B (100 µg/g) and Fluorescein (100 µg/g), all in a 12% carbamide gel (Example 5).
Figure 9B:
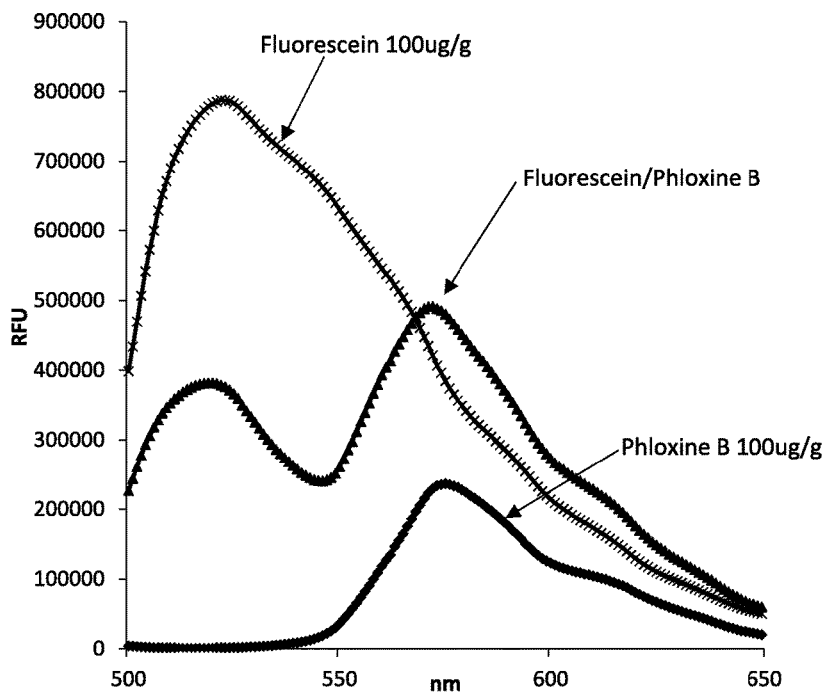

The absorption and emission spectra are shown in FIGS. 9A and 9B which indicate an energy transfer between the chromophores in the combination. For this particular combination of chromophores and at this concentration, for the chromophore combination two peaks corresponding to fluorescein and phloxine B emission was absorbed, with a higher peak at around 577 nm absorption, compared with the individual chromophores.

Example 6

Absorption/Emission Spectra of Fluorescein and Rose Bengal in a Gel

The photodynamic properties of (i) Fluorescein at about 100 µg/g final concentration, (ii) Rose Bengal at about 100 µg/g, and (iii) a mixture of Fluorescein (100 µg/g) and Phloxine B (100 µg/g), all in a 12% carbamide gel were evaluated. A flexstation 384 II spectrophotometer was used to measure emitted fluorescence with the following parameters: mode fluorescence, excitation 460 nm, emission spectra 465-750 nm. The absorbance was read using a synergy HT microplate reader: mode absorbance; spectra between 300-650 nm.

Figure 10A:
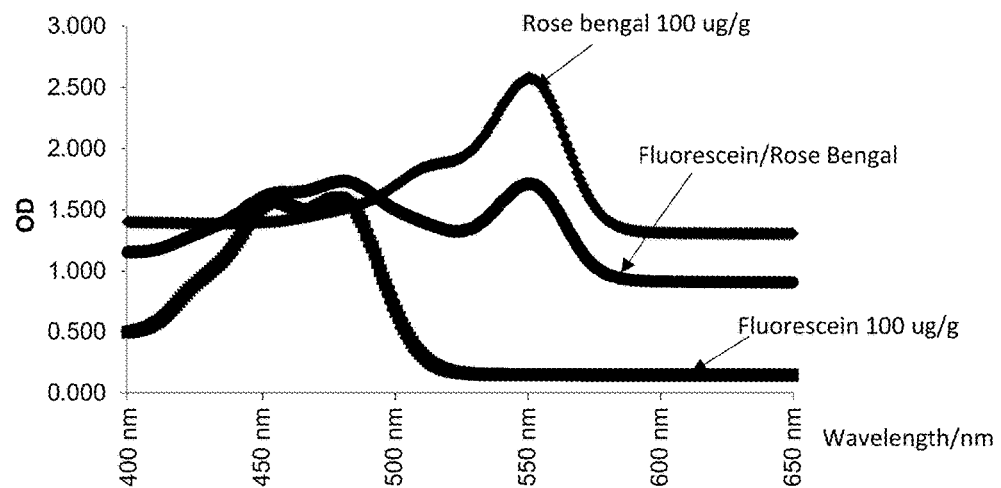
FIGS. 10A and 10B are absorbance and emission spectra, respectively, of (i) Phloxine B at 100 µg/g, (ii) Fluorescein at about 100 µg/g, and (iii) a mixture of Phloxine B (100 µg/g) and Fluorescein (100 µg/g), all in a 12% carbamide gel (Example 6).
Figure 10B:
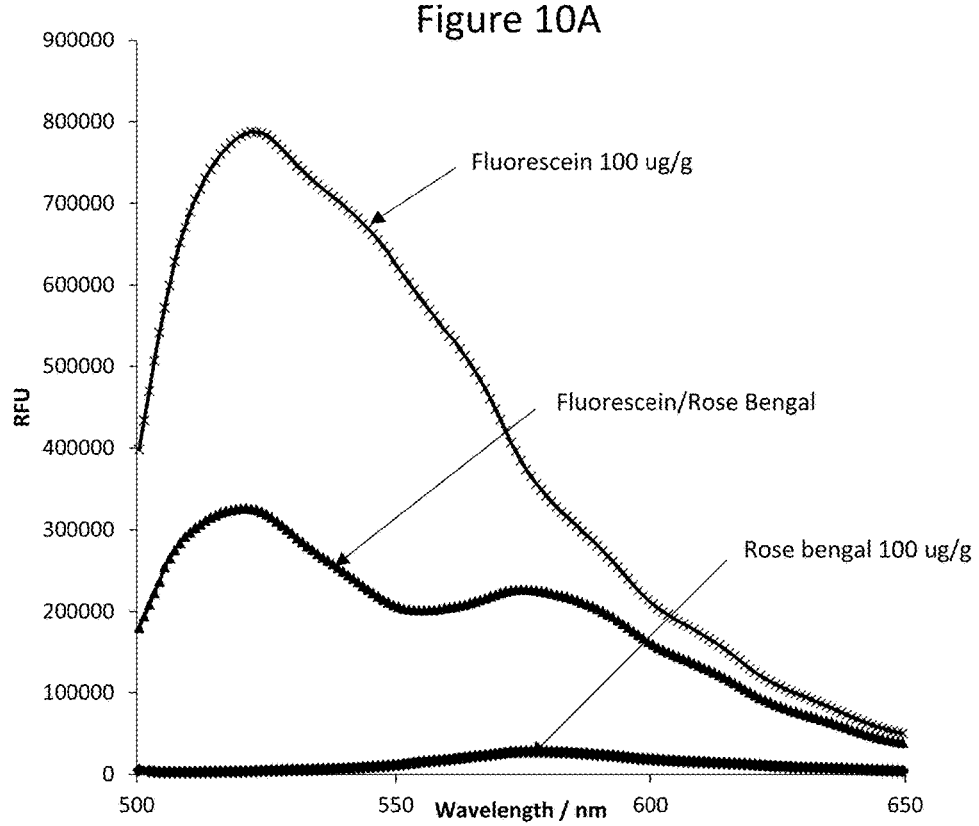

The absorption and emission spectra are shown in FIGS. 10A and 10B which indicate an energy transfer between the chromophores in the combination. For this particular combination of chromophores and at this concentration, two emission peaks were observed in the combined chromophore composition with the combined composition having a higher peak at around 580 nm, compared with the individual chromophores.

Example 7

Absorption/Emission Spectra of Rose Bengal and Eosin Y in a Gel

The photodynamic properties of (i) Eosin Y at 0.305 mg/mL final concentration, (ii) Rose Bengal at about 0.085 mg/mL, and (iii) a mixture of Eosin Y (0.305 mg/mL) and Rose Bengal (0.085 mg/mL), all in a 12% carbamide gel were evaluated. A flexstation 384 II spectrophotometer was used to measure emitted fluorescence with the following parameters: mode fluorescence, excitation 460 nm, emission spectra 465-750 nm. The absorbance was read using a synergy HT microplate reader: mode absorbance; spectra between 300-650 nm.

Figure 11A:
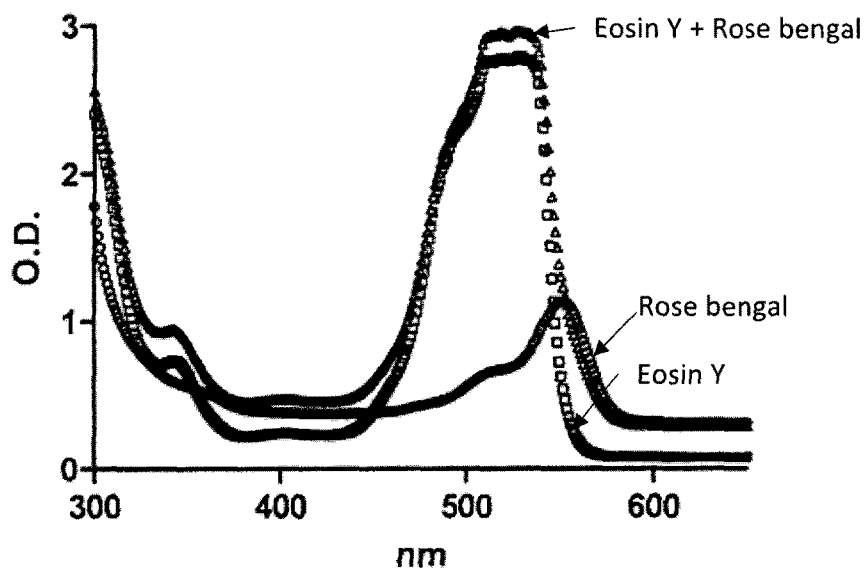
FIGS. 11A and 11B are absorbance and emission spectra, respectively, of (i) Eosin Y at 0.305 mg/mL final concentration, (ii) Rose Bengal at about 0.085 mg/mL, and (iii) a mixture of Eosin Y (0.305 mg/mL) and Rose Bengal (0.085 mg/mL), all in a 12% carbamide gel (Example 7).
Figure 11B:
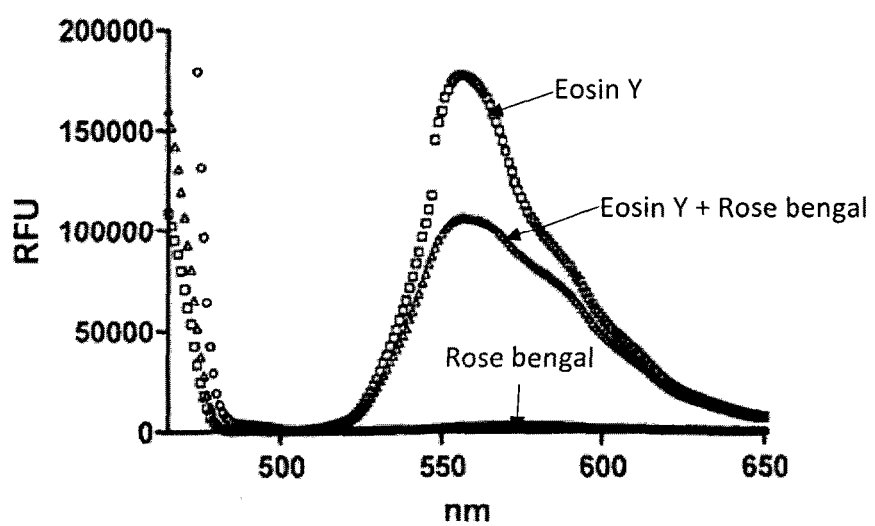

The absorption and emission spectra are shown in FIGS. 11A and 11B which indicate an energy transfer between the chromophores in the combination. For this particular combination of chromophores and at this concentration, a higher absorption was achieved with the chromophore combination, compared with the individual chromophores. The emission spectra of this specific combination had a lower power density than for Eosin Y alone. In the absence of a temperature rise in the composition during or after illumination, this apparent loss of energy may be attributed to reactive Oxygen species generation (see Example 8 below).

Example 8

Eosin and Rose Bengal Generate Oxygen Species

The synergy between two chromophores according to various embodiments of the present disclosure was investigated by preparing the following:
1—Eosin Y (0.035%)+Rose Bengal (0.085%) in a 12% carbamide gel.
2—Rose Bengal (0.085%) in a 12% carbamide gel.

Rose Bengal is known to have a high quantum yield in terms of singlet oxygen production in the presence of oxygen-releasing agents when photoactivated by green light (a singlet oxygen quantum yield of approximately 75% in water [Murasecco-Suardi et al, *Helvetica Chimica Acta*, Vol. 70, pp. 1760-73, 1987]). Eosin Y is known to have a high quantum yield in terms of emitted fluorescent light when photoactivated and can be at least partially activated by blue light when in a gel. Photoactivated Eosin Y has a much lower quantum yield in terms of singlet oxygen production in the presence of oxygen-releasing agents (a singlet oxygen quantum yield when fully activated of approximately 4% [Gandin et al, *Photochemistry and Photobiology*, Vol. 37, pp. 271-8, 1983]).

Figure 12:
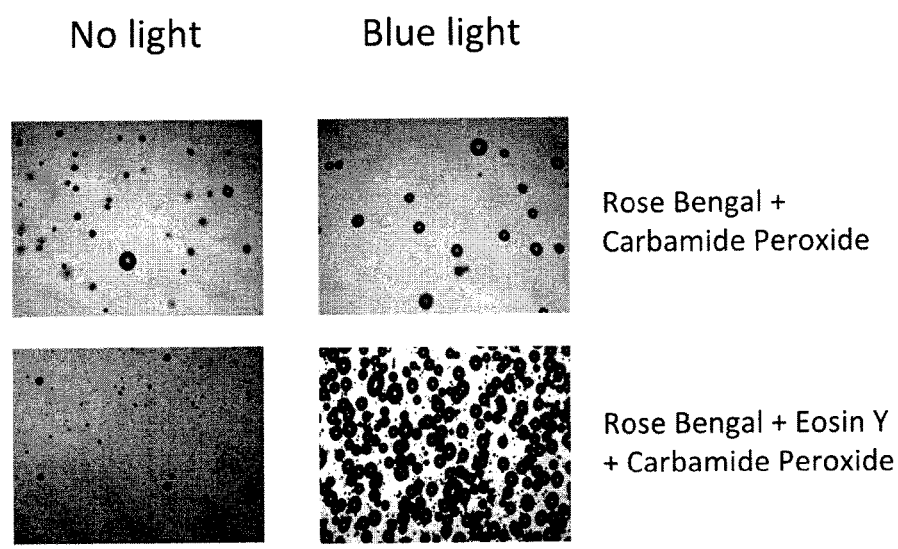
FIG. 12 shows that Eosin Y and Rose Bengal act in a synergistic manner (Example 8).

When Eosin Y and Rose Bengal are combined, it appears that both chromophores are activated by the same blue light as evidenced by FIG. 12.

FIG. 12, left panel, shows a photograph of the composition when viewed under a light microscope (×250) before exposure to an activating blue light. Very few bubbles were seen in both compositions. Following illumination with blue light a dramatic increase in bubbles was seen with the composition comprising a combination of Eosin Y and Rose Bengal, but not with the composition comprising Rose Bengal alone or Eosin Y alone (not shown). This suggests that there is a transfer of energy from Eosin Y to Rose Bengal leading to the formation oxygen species. Eosin Y alone in a carbamide gel presented similar properties to Rose Bengal. A similar effect was observed with Fluorescein and Rose Bengal.

Example 9

Variation of the Chromophore Concentration Ratios

The effect of varying the concentrations of the individual chromophores in multiple chromophore compositions, according to embodiments of the present disclosure, were investigated. The fluorescence emission over time of compositions comprising (i) Fluorescein—Eosin Y, and (ii) Eosin Y—Rose Bengal, are presented in FIGS. 13A and 13B respectively.

Figure 13A:
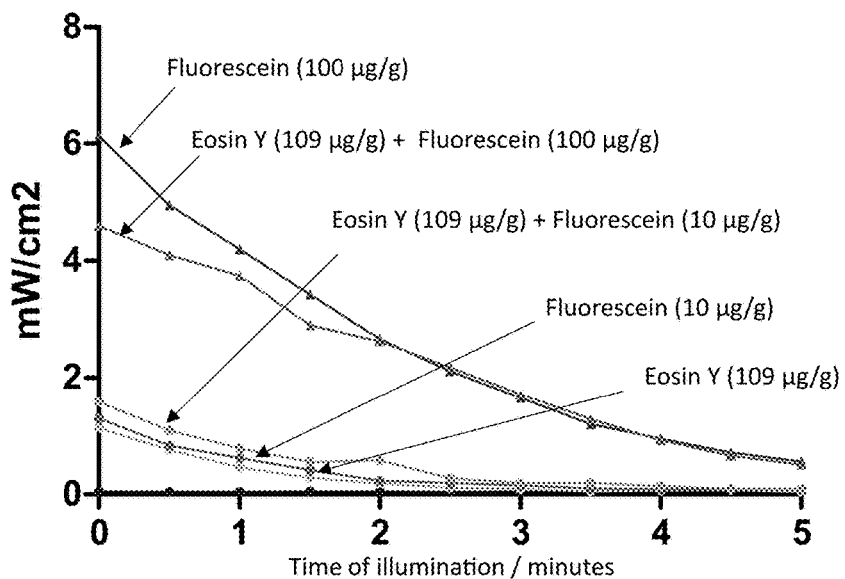
FIGS. 13A and 13B show the fluorescence emission (power density) over time of compositions comprising (i) Fluorescein+Eosin Y (FIG. 11A), and (ii) Eosin Y+Rose Bengal (FIG. 11B) (Example 9).

As can be seen in FIG. 13A, the emission properties of the following were investigated: (i) 109 µg/g of Eosin Y+10 µg/g of fluorescein, (ii) 109 µg/g of Eosin Y+100 µg/g of fluorescein, (iii) 109 µg/g of Eosin Y, (iv) 10 µg/g of fluorescein, (v) 100 µg/g of fluorescein, all in a carbamide peroxide gel. An SP-100 spectroradiometer was used to measure the power density spectra (mW/cm$^2$ versus wavelength) of a photonic signal detected from the various compositions when illuminated with blue light (wavelength of about 440 to 480 nm at a power density of less than 150 mW/cm$^2$ for about 5 minutes). Fluorescence is measured as light within the 519-700 nm range.

As can be seen, the emitted fluorescence of all concentrations decay over time. This decay is often accompanied by a photobleaching of one or more of the chromophores in the composition. A higher concentration of fluorescein in a multiple chromophore composition provides a higher initial emitted fluorescence which also lasts longer, i.e. has a longer lifetime. For the Eosin Y (109 µg/g) and Fluorescein (100 µg/g) composition, the initial emitted fluorescence is slightly lower than that of a composition comprising 100 µg/g fluorescein alone. This may be attributed to use of energy to form oxygen species (as described in Example 6 above). Therefore, the relative concentrations of the chromophores within a multiple chromophore composition can be varied to tailor the resultant fluorescence and oxygen species properties.

Figure 13B:
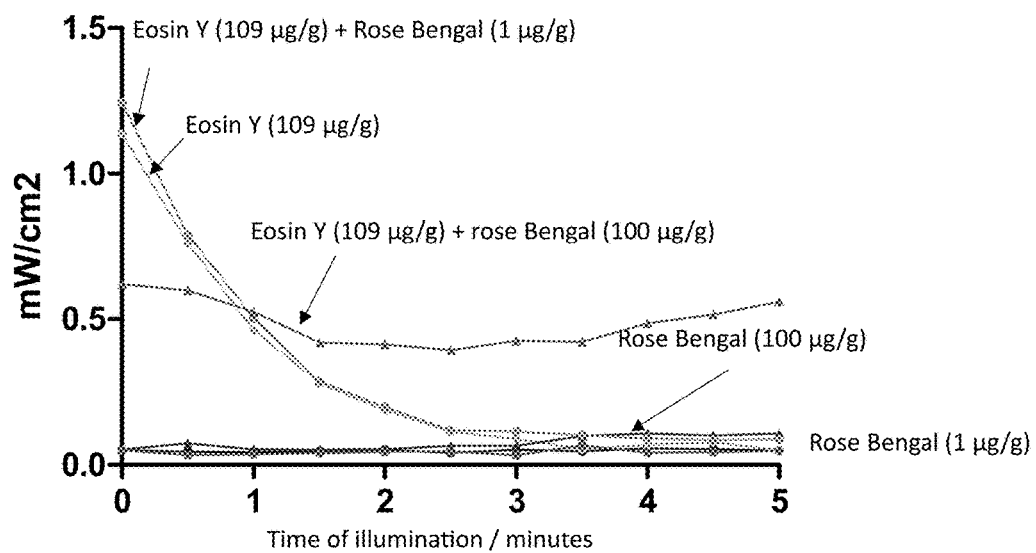

In FIG. 13B, the following compositions were evaluated (i) 109 µg/g of Eosin Y+1 µg/g of rose bengal (ratio of about 10:1), (ii) 109 µg/g of Eosin Y+100 µg/g of rose bengal (ratio of about 1:1), (iii) 109 µg/g of Eosin Y, (iv) 1 µg/g of rose bengal, (v) 100 µg/g of rose bengal, all in a carbamide peroxide gel. The same decay trend observed in FIG. 13A was also observed for eosin Y alone, eosin Y-1 µg/g rose bengal, as well as eosin Y-10 µg/g rose Bengal (not shown). The very low fluorescence levels for both concentrations of rose bengal alone when activated by blue light can also be observed. Surprisingly, for the composition of 109 µg/g of Eosin Y+100 µg/g of rose bengal a sustained fluorescence was observed, albeit at a lower level than that of Eosin Y alone, and Eosin Y+1 µg/g of rose bengal. In this composition, no photobleaching of Eosin Y was observed. Without wishing to be limited by theory, it is believed that Eosin Y is not photobleaching as at this ratio of Eosin Y/rose Bengal, Eosin Y is able to transfer all of its absorbed energy to rose bengal which then emits the energy and thus prevents the photodegradation of the eosin Y molecules. The peak emission wavelength of the 109 µg/g Eosin Y+100 µg/g rose bengal composition is closer to that of rose bengal's peak emission wavelength than that of eosin y.

A similar sustained fluorescence effect was observed for a composition comprising fluorescein, eosin Y and rose bengal at relative concentration ratios of about 1:10:10 (not shown).

Example 10

Absorption/Emission Spectra of Fluorescein, Eosin Y and Rose Bengal in a Gel

The photodynamic properties of (i) Rose Bengal at about 0.085 mg/mL, (ii) Fluorescein sodium salt at about 0.44 mg/mL final concentration, (ii) Eosin Y at about 0.305 mg/mL, and (iii) a mixture of (i), (ii) and (iii) according to an embodiment of the present disclosure in a gel comprising about 12% carbamide peroxide were evaluated. A flexstation 384 II spectrophotometer was used to measure emitted fluorescence with the following parameters: mode fluorescence, excitation 460 nm, emission spectra 465-750 nm. The absorbance was read using a synergy HT microplate reader: mode absorbance; spectra between 300-650 nm.

Figure 14A:
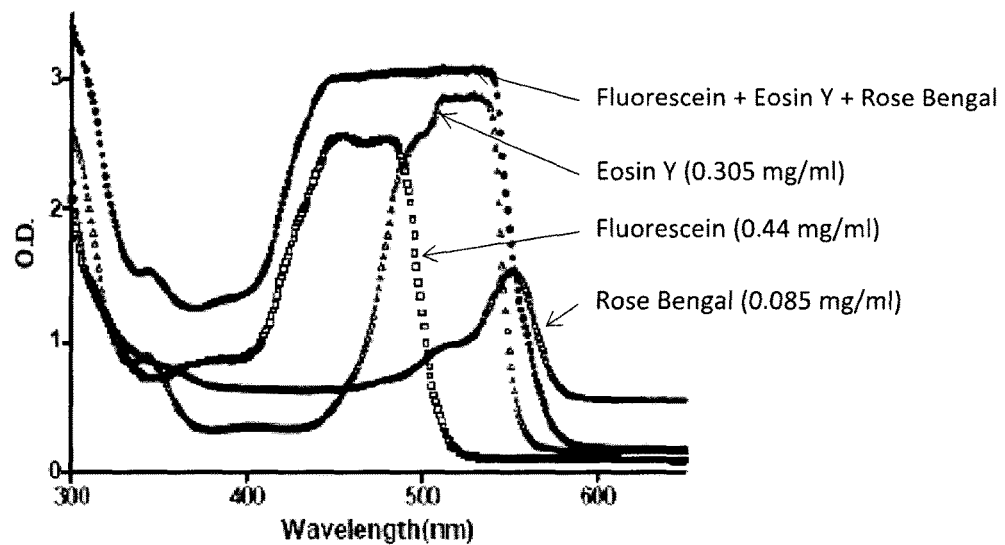
FIGS. 14A and 14B are absorbance and emission spectra, respectively, of (i) Rose Bengal at about 0.085 mg/mL, (ii) Fluorescein sodium salt at about 0.44 mg/mL final concentration, (iii) Eosin Y at about 0.305 mg/mL, and (iii) a mixture of (i), (ii) and (iii) in a carbamide gel (Example 10).
Figure 14B:
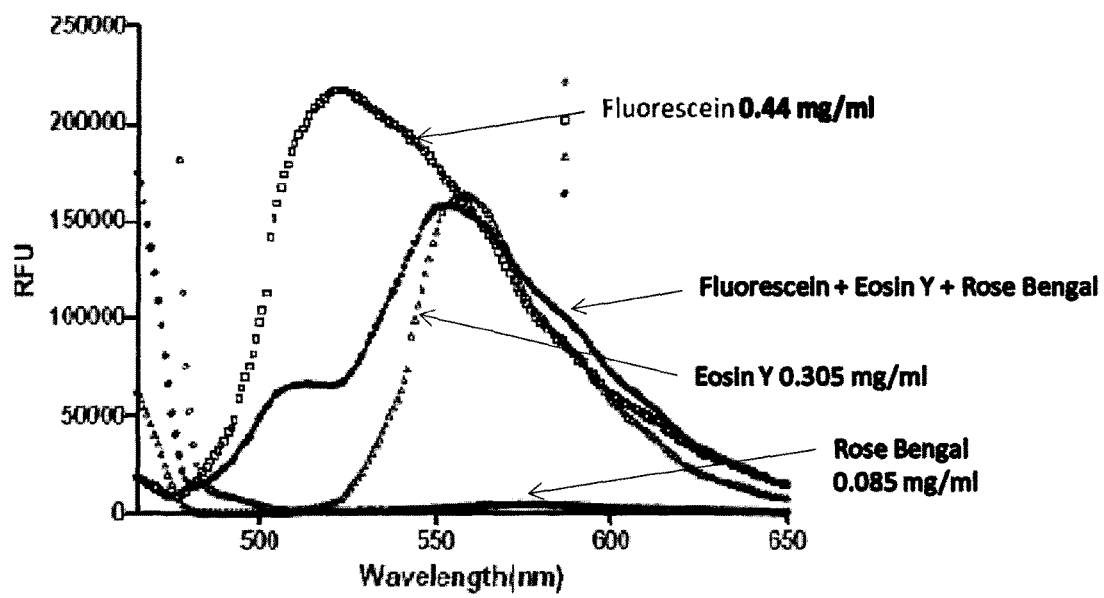

The absorbance and emission spectra are shown in FIGS. 14A and 14B which indicate an energy transfer between the chromophores in the chromophore combination. As is clear from FIG. 14B, the bandwidth of the Fluorescein, Eosin Y and Rose Bengal combination is wider than that of Eosin Y alone.

Example 11

Absorption/Emission Spectra of Fluorescein, Eosin Y and Rose Bengal in an Aqueous Solution The photodynamic properties of (i) Rose Bengal at about 0.085 mg/mL, (ii) Fluorescein sodium salt at about 0.44 mg/mL final concentration, (ii) Eosin Y at about 0.305 mg/mL, and (iii) a mixture of (i), (ii) and (iii) in an aqueous solution according to an embodiment of the present disclosure were evaluated. A flexstation 384 II spectrophotometer was used to measure emitted fluorescence with the following parameters: mode fluorescence, excitation 460 nm, emission spectra 465-750 nm. The absorbance was read using a synergy HT microplate reader: mode absorbance; spectra between 300-650 nm.

Figure 15A:
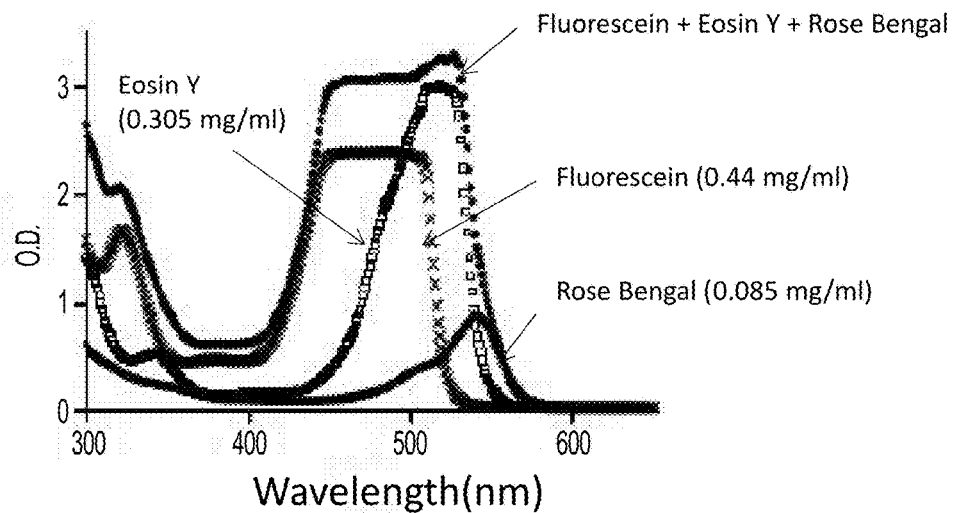
FIGS. 15A and 15B are absorbance and emission spectra, respectively, of (i) Rose Bengal at about 0.085 mg/mL, (ii) Fluorescein sodium salt at about 0.44 mg/mL final concentration, (ii) Eosin Y at about 0.305 mg/mL, and (iii) a mixture of (i), (ii) and (iii) in an aqueous composition (Example 11).
Figure 15B:
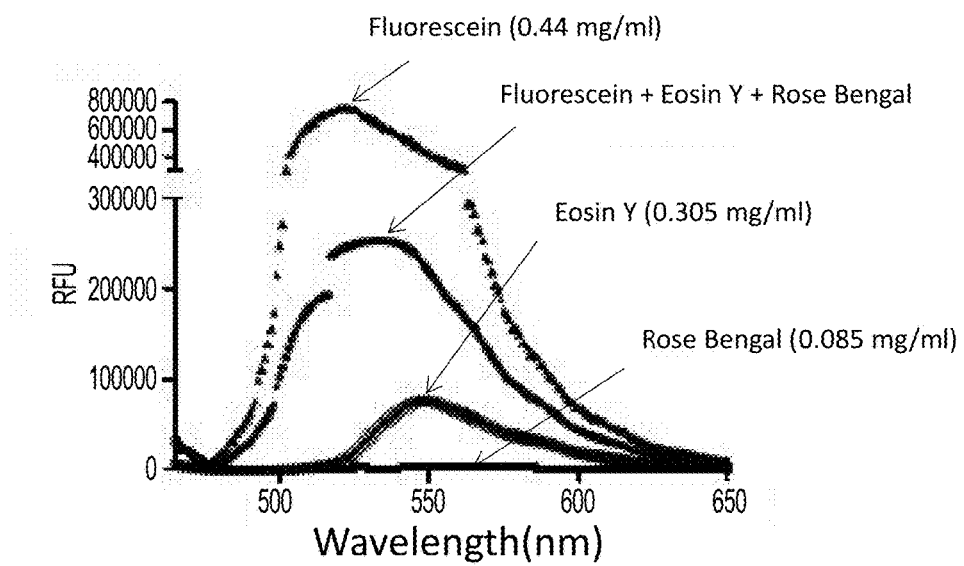

The absorbance and emission spectra are shown in FIGS. 15A and 15B which indicate an energy transfer between the chromophores in the chromophore combination, in the absence of a peroxide but in the presence of other oxygen-releasing agents (e.g. water).

In reference to the absorption and emission spectra of the compositions of the present disclosure within a carbamide peroxide gel, the same spectra was obtained for the same chromophores in a gel without the peroxide.

Example 12

Angiogenic Potential of a Composition of the Disclosure

A human skin model was developed to assess the angiogenic potential of compositions of the present disclosure. Briefly, a composition comprising Eosin Y and Erythrosine was placed on top of a human skin model containing fibroblasts and keratinocytes. The skin model and the composition were separated by a nylon mesh of 20 micron pore size. The composition was then irradiated with blue light ('activating light') for 5 minutes at a distance of 5 cm from the light source. The activating light consisted of light emitted from an LED lamp having an average peak wavelength of about 400-470 nm, and a power intensity measured at 10 cm of 7.7 J/cm$^2$ to 11.5 J/cm$^2$. Upon illumination with the activating light, the composition emitted fluorescent light. Since the composition was in limited contact with the cells, the fibroblasts and keratinocytes were exposed mainly to the activating light and the fluorescent light emitted from the composition. Conditioned media from the treated human 3D skin model were then applied to human aortic endothelial cells previously plated in Matrigel®. The formation of tubes by endothelial cells was observed and monitored by microscopy and image analysis after 24 hours. The conditioned media from 3D skin models treated with light illumination induced endothelial tube formation in vitro, suggesting an indirect effect of the light treatment (blue light and fluorescence) on angiogenesis via the production of factors by fibroblasts and keratinocytes. Plain media and conditioned media from untreated skin samples were used as a control, and did not induce endothelial tube formation.

Figure 16:
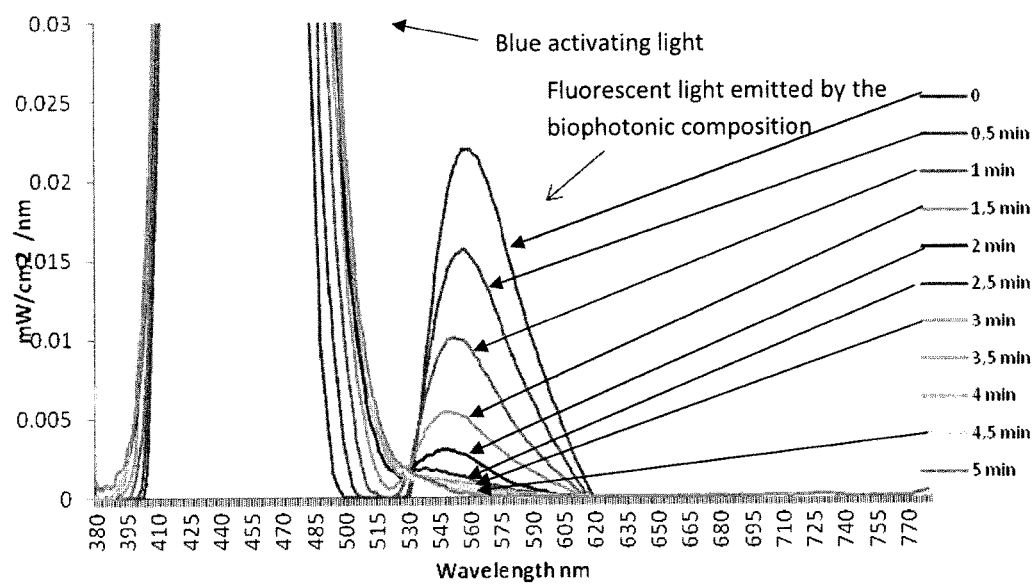
FIG. 16 is an emission spectrum showing the intensity over time of the light being emitted from the composition tested in Examples 12 and 13.

FIG. 16 is an emission spectrum showing the intensity over time of the light being emitted from the biophotonic composition as measured using the spectroradiometer of Example 9. It can be reasonably inferred that other chromophore combinations exhibiting a comparable emission spectra would also induce angiogenesis. As can be seen from FIG. 16, the emitted fluorescence light had a wavelength of about 520-620 nm with a peak at around 560 nm. Similar emission spectra were observed using Eosin Y and Fluorescein (FIG. 5B); Eosin Y and Phloxine B (FIG. 7B, FIG. 8B); Eosin Y and Rose Bengal (FIG. 11B); Fluorescein, Eosin Y and Rose bengal (FIG. 14B, FIG. 15B). Other chromophore combinations with similar emission spectra are also possible, which can be reasonably expected to have angiogenic properties.

Example 13

Protein Secretion and Gene Expression Profiles

Wounded and unwounded 3D human skin models (EpiDermFT, MatTek Corporation) were used to assess the potential of a composition of the present disclosure to trigger distinct protein secretion and gene expression profiles. Briefly, a composition comprising Eosin and Erythrosine were placed on top of wounded and unwounded 3D human skin models cultured under different conditions (with growth factors (1x), 50% growth factors (0.5x) and no growth factors (0x)). The different conditions mimicked non-compromised healing, semi-starvation conditions and starvations conditions, respectively. The skin models and the composition were separated by a nylon mesh of 20 micron pore size. Each skin model-composition combination was then irradiated with blue light ('activating light') for 5 minutes at a distance of 5 cm from the light source. The activating light consisted of light emitted from an LED lamp having an average peak wavelength of about 440-470 nm, a power density of 60-150 mW/cm$^2$ at 5 cm, and a total energy density after 5 minutes of about 18-39 J/cm$^2$. The controls consisted of 3D skin models not illuminated with light.

Gene expression and protein secretion profiles were measured 24 hours post-light exposure. Cytokine secretion was analyzed by antibody arrays (RayBio Human Cytokine antibody array), gene expression was analyzed by PCR array (PAHS-013A, SABioscience) and cytotoxicity was determined by GAPDH and LDH release. Results (Tables 1 and 2) showed that the light treatment is capable of increasing the level of protein secreted and gene expression involved in the early inflammatory phase of wound healing in wounded skin inserts and in non-starvation conditions. In starvation conditions mimicking chronic wounds, there was no increase in the level of inflammatory protein secreted when compared to the control. Interestingly, the effect of the light treatment on unwounded skin models has a much lower impact at the cellular level than on wounded skin insert, which suggests an effect at the cellular effect level of the light treatment. It seems to accelerate the inflammatory phase of the wound healing process. Due to the lack of other cell types such as macrophages in the 3D skin model, the anti-inflammatory feed-back is absent and may explain the delay in wound closure. Cytotoxicity was not observed in the light treatments. The eosin y and erythrosine b composition had the same emission properties as illustrated in FIG. 16. As stated above, it can be reasonably inferred that other chromophore combinations exhibiting a comparable emission spectra would also induce secretion of proteins or gene expression as seen in this Example.

TABLE 1

List of proteins with statistically significant difference secretion ratio between treated and untreated control at day 3. Two arrows mean that the ratio was over 2 folds.

|  | Medium 1X | Medium 0.5X | Medium 0X |
|---|---|---|---|
| Increase |  | ENA78<br>p = 0.04<br>IL-1R4/ST2<br>p = 0.02<br>MMP3 p = 0.01<br>MCP-2 p = 0.04 | ↑↑ Angiogenin ↑<br>p = 0.03<br>↑↑ CXCL16 ↑<br>p = 0.04<br>↑↑<br>↑↑ |
| Decrease | BMP6 ↓<br>p = 0.01<br>TNFα ↓<br>p = 0.005 | BMP6 p = 0.02 ↓ |  |

TABLE 2

List of genes with statistically significant difference expression ratio between treated and untreated control during the first 24 hours. Two arrows mean that the ratio was over 2 folds.

| | Medium 1X | | Medium 0.5X | | Medium 0X | |
|---|---|---|---|---|---|---|
| Increase | CTGF p = 0.02 | ↑ | CTGF P = 0.04 | ↑ | MMP3 p = 0.007 | ↑↑ |
| | ITGB3 p = 0.03 | ↑ | ITGB3 p = 0.05 | ↑ | LAMA1 p = 0.03 | ↑ |
| | MMP1 p = 0.03 | ↑ | MMP1 p = 0.02 | ↑↑ | ITGA2 p = 0.03 | ↑ |
| | MMP3 p = 0.01 | ↑ | MMP10 p = 0.003 | ↑↑ | | |
| | THBS1 P = 0.02 | ↑ | MMP3 p = 0.007 | ↑↑ | | |
| | | | MMP8 p = 0.02 | ↑↑ | | |
| | | | THBS1 p = 0.03 | ↑ | | |
| Decrease | HAS1 p = 0.009 | ↓↓ | NCAM1 p = 0.02 | ↓↓ | | |
| | NCAM1 p = 0.05 | ↓↓ | VCAN p = 0.02 | ↓ | | |
| | VCAM1 p = 0.03 | ↓↓ | LAMC1 p = 0.002 | ↓ | | |
| | COL7A1 p = 0.04 | ↓ | COL6A1 p = 0.007 | ↓ | | |
| | CTNNA1 p = 0.03 | ↓ | MMP7 p = 0.003 | ↓ | | |

Example 14

Eosin Y and Fluorescein Induce Collagen Formation

A composition according to an embodiment of the present invention, comprising 0.01% Eosin Y and 0.01% Fluorescein in a carrier matrix (1.8% carbopol gel) was evaluated for its potential to induce collagen formation. Dermal human fibroblasts were plated in glass-bottomed dishes with wells (MatTek®). There were approximately 4000 cells per well. After 48 hours, the glass-bottomed dishes were inverted and the cells were treated through the glass bottom with (i) a no light (control), (ii) sunlight exposure for about 13 minutes at noon (control), (iii) the composition applied to the glass well bottom on the other side of the cells (no light exposure), (iv) the composition applied to the glass well bottom on the other side of the cells (sun light exposure for about 13 minutes at noon), and (v) the composition applied to the glass well bottom on the other side of the cells (blue light exposure for about 5 minutes). In the case of (iii), (iv) and (v), there was no direct contact between the cells and the composition. In the case of (iv) and (v), the cells were exposed to emitted light from and through the Eosin Y and Fluorescein composition when exposed to sunlight and blue light respectively. An at least partial photobleaching was observed in (iv) and (v). After the treatment, the cells were washed and incubated in regular medium for 48 hours. A collagen assay was then performed on the supernatant using the Picro-Sirius red method. This involved adding Sirius red dye solution in picric acid to the supernatant, incubating with gentle agitation for 30 minutes followed by centrifugation to form a pellet. The pellet was washed first with 0.1N HCl and then 0.5 N NaOH to remove free dye. After centrifugation, the suspension was read at 540 nm for collagen type I. The results are shown in Table 1.

TABLE 1

A qualitative comparison of collagen type I concentration in a dermal human fibroblast supernatant exposed to (i) a no light (control), (ii) sunlight exposure for about 13 minutes at noon (control), (iii) any light emitted from a Eosin Y and Fluorescein composition through a glass separation (no light exposure), (iv) any light emitted from a Eosin Y and Fluorescein composition through a glass separation (sun light exposure for about 13 minutes at noon), and (v) the composition applied to the glass well bottom on the other side of the cells (blue light exposure for about 5 minutes).

| | No light (control) | Sunlight (control) | Eosin Y + Fluorescein - no light | Eosin and Fluorescein - sunlight | Eosin and Fluorescein - blue light |
|---|---|---|---|---|---|
| Collagen concentration | + | + | ++ | +++ | +++ |

++ indicates collagen levels about twice as high as +, and +++ indicates collagen levels about three times as high as +.

There was a statistical difference between the collagen levels induced by the Eosin Y and Fluorescein composition exposed to sunlight and blue light compared to the no light and sunlight alone controls.

Collagen generation is indicative of a potential for tissue repair including stabilization of granulation tissue and decreasing of wound size. It is also linked to reduction of fine lines, a decrease in pore size, improvement of texture and improvement of tensile strength of intact skin. The emission spectra of the Eosin Y and Fluorescein composition of this example had a single peak emission with a wavelength that ranged from about 480-620 nm. Following illumination with sunlight, the power density of the peak was reduced indicating an at least partial photobleaching in 13 minutes, which was also observed by a change in colour of the composition. The rate of fluorescence emission/photobleaching was slower when illuminated by sunlight (white light) compared to Eosin Y and Fluorescein compositions (e.g. compositions of Examples 5 and 6) when activated by blue light.

Example 15

Selecting the Concentration of Chromophore in the Biophotonic Composition

Figure 17A:
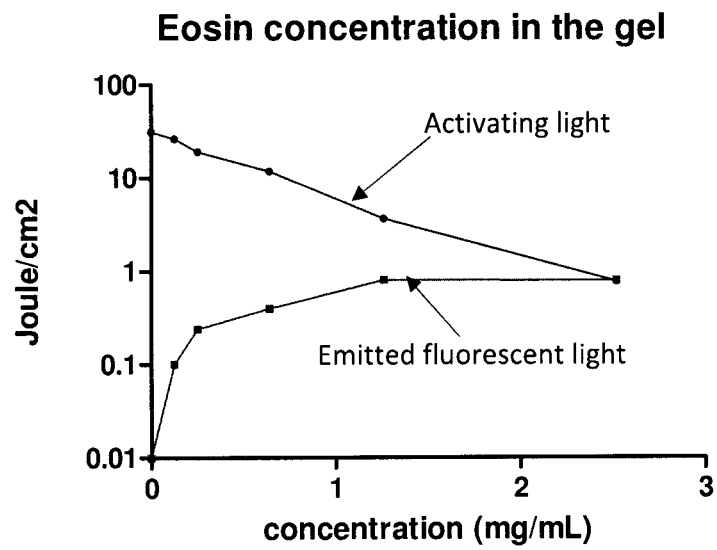
FIGS. 17A and 17B show that the energy density of emitted fluorescence from Eosin (top) and Fluorescein (bottom) in a composition increases rapidly with increasing chromophore concentration but slows down to a plateau with further concentration increase, whilst the activating light decreases with increasing concentration (Example 15).
Figure 17B:
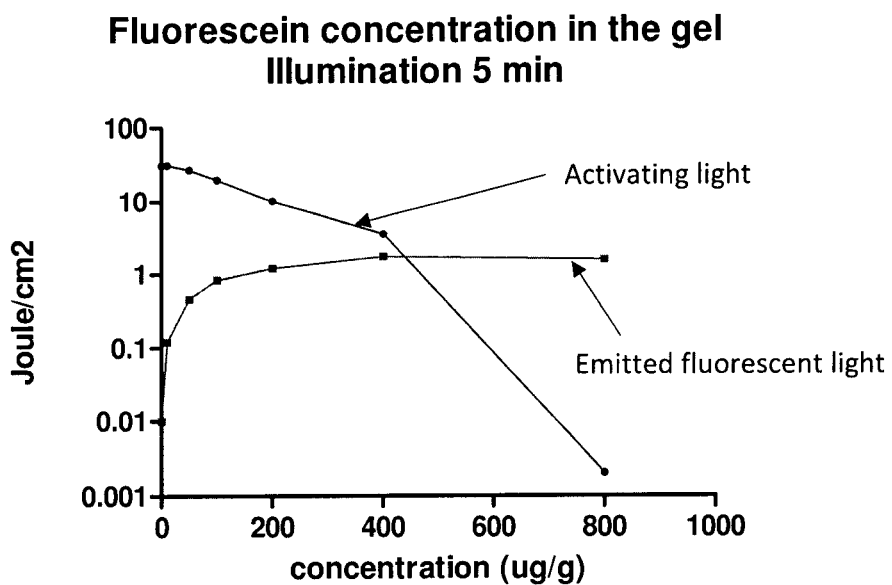

The fluorescence spectra of compositions with different concentrations of chromophores were investigated using a spectroradiometer and an activating blue light (as in Example 9). Exemplary fluorescence spectra of Eosin Y and Fluorescein are presented in FIGS. 17A and 17B. It was found that emitted fluorescence from the chromophore increases rapidly with increasing concentration but slows down to a plateau with further concentration increase. Activating light passing through the composition decreases with increasing chromophore composition as more is absorbed by the chromophores. Therefore, the concentration of chromophores in compositions of the present disclosure can be selected according to a required ratio and level of activating light and fluorescence treating the tissue based on this example. In some embodiments, it will be after the zone of rapid increase, i.e. between 0.5 and 1 mg/mL for Eosin Y (FIG. 17A).

Therefore, concentration can be selected according to required activating light and fluorescence. In some embodiments, it will be after zone of rapid increase, i.e. between 0.5 and 1 mg/mL for Eosin Y (FIG. 17A).

Compositions with rose bengal behave slightly differently and become more opaque with increasing concentration which may be due to bubble formation.

Similarly, the relationship between the power density of light received by the tissues with illuminating time was investigated. It was found that the power density of the activating light was low initially and increased with time. This correlates with the light absorbing chromophores photobleaching and more of the activating light passing through the composition to reach tissues. In parallel, the fluorescent light emitted by the composition decreased with time as one or more of the chromophores photobleached. Overall, the total power density of the light treating the tissues increased gradually over illumination time.

It should be appreciated that the invention is not limited to the particular embodiments described and illustrated herein but includes all modifications and variations falling within the scope of the invention as defined in the appended claims.

What is claimed is:

1. A biophotonic composition for topical application to a target tissue, the biophotonic composition comprising a first xanthene dye and at least one other xanthene dye, wherein the first xanthene dye is Eosin Y and is present in the biophotonic composition at a concentration of between about 0.5 mg/mL and about 1 mg/mL; and wherein the at least one other xanthene dye is present in the biophotonic composition at a concentration of between about 0.001% and about 0.5% per weight of the biophotonic composition.

2. The biophotonic composition of claim 1, wherein the at least one other xanthene dye is selected from the group consisting of Fluorescein and Rose Bengal.

3. The biophotonic composition of claim 1, wherein activation by light results in a cascade of energy transfer between Eosin Y and the at least one other xanthene dye.

4. The biophotonic composition of claim 1, wherein Eosin Y absorbs at a wavelength in the range of the visible spectrum.

5. The biophotonic composition of claim 1, wherein Eosin Y absorbs at a wavelength of between about 400-600 nm.

6. The biophotonic composition of claim 1, wherein the at least one other xanthene dye absorbs at a wavelength that is relatively longer than that of Eosin Y within the range of between about 10-100 nm.

7. The biophotonic composition of claim 1, wherein Eosin Y and the at least one other xanthene dye are present in the biophotonic composition at a concentration of between about 0.001-0.1% or between about 0.001-0.01% per weight of the biophotonic composition.

8. A method for biophotonic treatment of a skin disorder comprising:
    topically applying a biophotonic composition to a target tissue, the composition comprising Eosin Y present in the biophotonic composition at a concentration of between about 0.5 mg/mL and about 1 mg/mL and at least one other xanthene dye; and
    illuminating said biophotonic composition with light having a wavelength that overlaps with an absorption spectrum of Eosin Y, wherein the at least one other xanthene dye is selected from the group consisting of Fluorescein and Rose Bengal, and wherein Eosin Y and the at least one other xanthene dye are present in the biophotonic composition at a concentration of between about 0.001% and about 0.5% per weight of the biophotonic composition.

9. The method of claim 8, wherein said biophotonic composition promotes collagen synthesis.

10. The method of claim 8, wherein said biophotonic composition reduces inflammation.

11. The method of claim 8, wherein said biophotonic composition reduces the formation of scar tissue.

12. The method of claim 8, wherein the biophotonic composition is illuminated for a period of at least 3 minutes.

13. The method of claim 8, wherein the application of light results in a cascade of energy transfer between the chromophores.

14. The method of claim 13, wherein the cascade of energy transfer does not result in tissue damage.

15. The method of claim 8, wherein Eosin Y dye absorbs at a wavelength of between about 200-600 nm.

16. The method of claim 8, wherein Eosin Y and the at least one other xanthene dye are present in an amount of between about 0.01-0.5%, between about 0.001-0.1%, or between about 0.001-0.01% per weight of the biophotonic composition.

* * * * *